United States Patent
Shimada

(10) Patent No.: US 11,266,822 B2
(45) Date of Patent: Mar. 8, 2022

(54) MICRONEEDLE ARRAY

(71) Applicant: FUJIFILM Corporation, Tokyo (JP)

(72) Inventor: Toshio Shimada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/158,942

(22) Filed: Oct. 12, 2018

(65) Prior Publication Data

US 2019/0076635 A1 Mar. 14, 2019

Related U.S. Application Data

(63) Continuation of application No. PCT/JP2017/014963, filed on Apr. 12, 2017.

(30) Foreign Application Priority Data

Apr. 15, 2016 (JP) .............................. JP2016-081778

(51) Int. Cl.
| | |
|---|---|
| *A61M 37/00* | (2006.01) |
| *A61K 47/02* | (2006.01) |
| *A61K 47/24* | (2006.01) |
| *A61K 9/70* | (2006.01) |
| *A61K 47/36* | (2006.01) |

(52) U.S. Cl.
CPC ........... *A61M 37/0015* (2013.01); *A61K 9/70* (2013.01); *A61K 47/02* (2013.01); *A61K 47/24* (2013.01); *A61K 47/36* (2013.01); *A61M 37/00* (2013.01); *A61M 2037/003* (2013.01); *A61M 2037/0023* (2013.01)

(58) Field of Classification Search
None
See application file for complete search history.

(56) References Cited

U.S. PATENT DOCUMENTS

| | | | | |
|---|---|---|---|---|
| 8,758,810 | B2* | 6/2014 | Okada | A61P 35/00 424/450 |
| 2002/0082543 | A1* | 6/2002 | Park | A61B 5/1411 604/21 |
| 2004/0049150 | A1 | 3/2004 | Dalton et al. | |
| 2004/0087893 | A1 | 5/2004 | Kwon | |
| 2005/0197308 | A1 | 9/2005 | Dalton et al. | |
| 2006/0034902 | A1 | 2/2006 | Cormier et al. | |
| 2007/0207194 | A1 | 9/2007 | Grayburn et al. | |
| 2008/0269685 | A1 | 10/2008 | Singh et al. | |
| 2011/0274625 | A1 | 11/2011 | Redelmeier et al. | |
| 2012/0010557 | A1 | 1/2012 | Heger | |
| 2014/0066842 | A1* | 3/2014 | Zhang | A61K 9/0021 604/46 |
| 2014/0200509 | A1* | 7/2014 | Cohen | A45D 34/04 604/46 |
| 2014/0294919 | A1 | 10/2014 | Dalton et al. | |
| 2014/0356416 | A1* | 12/2014 | Kesari | A61K 31/704 424/450 |
| 2015/0202153 | A1* | 7/2015 | Frank | A61K 31/4745 424/450 |
| 2015/0238413 | A1* | 8/2015 | Mochizuki | A61K 9/0021 264/510 |

FOREIGN PATENT DOCUMENTS

| | | |
|---|---|---|
| CN | 101389273 A | 3/2009 |
| CN | 102256596 A | 11/2011 |
| CN | 102300557 A | 12/2011 |
| CN | 104083759 A | 10/2014 |
| CN | 104812372 A | 7/2015 |
| JP | 60-13718 A | 1/1985 |
| JP | 2004-504120 A | 2/2004 |
| JP | 2008-509747 A | 4/2008 |
| JP | 2014-507473 A | 3/2014 |
| JP | 2015-521910 A | 8/2015 |
| JP | 2016-030072 A | 3/2016 |
| WO | 2013/152092 A1 | 10/2013 |

OTHER PUBLICATIONS

International Preliminary Report on Patentability and translation of Written Opinion issued from the International Bureau in counterpart International Application No. PCT/JP2017/014963, dated Oct. 16, 2018.
Written Opinion issued by the International Searching Authority in corresponding International Application No. PCT/JP2017/014963, dated Jul. 18, 2017.
International Search Report issued by the International Searching Authority in corresponding International Application No. PCT/JP2017/014963, dated Jul. 18, 2017.
Lei Guo et al., "Enhanced transcutaneous immunization via dissolving microneedle array loaded with liposome encapsulated antigen and adjuvant", International Journal of Pharmaceutics, vol. 447, 2013 (pp. 22-30).

(Continued)

*Primary Examiner* — Celeste A Roney
(74) *Attorney, Agent, or Firm* — Sughrue Mion, PLLC

(57) ABSTRACT

An object of the present invention is to provide a microneedle array which is capable of suppressing aggregation of liposomes in a case where a water-soluble polymer is mixed with liposomes during production of the microneedle array and is capable of localizing a drug at a tip of a needle. According to the present invention, provided is a microneedle array including: a sheet; and a plurality of needles which are present on an upper surface of the sheet, in which each needle contains a water-soluble polymer, a drug, a liposome, and a salt, a zeta potential of the liposome is −10 mV or less, the zeta potential is a zeta potential of a liquid obtained by diluting the liposome to 0.1 mg/mL with 10 mmol/L of a phosphoric acid aqueous solution having a pH of 7, and a content of the salt in a portion of each needle which contains the liposome is 2.5 mmol/g or less.

16 Claims, 12 Drawing Sheets

(56) References Cited

OTHER PUBLICATIONS

Office Action dated Mar. 15, 2019 from the Australian Government Patent Office in Australian Application No. 2017251040.
Office Action dated Jul. 9, 2019, from the Japanese Patent Office in counterpart Japanese application No. 2018-512044.
Extended European Search Report dated Feb. 26, 2019, from the European Patent Office in counterpart European Application No. 17782427.3.
Office Action dated Feb. 7, 2020 from the European Patent Office in EP Application No. 17782427.3.
Office Action dated Jul. 13, 2020 from the State Intellectual Property Office of the P.R.C. in Chinese Application No. 201780023704.2.
Office Action dated Jun. 25, 2020 from the Korean Intellectual Property Office in KR Application No. 10-2018-7029483.
Office Action dated Feb. 5, 2021 from the China National Intellectual Property Administration in CN Application No. 201780023704.2.

* cited by examiner

FIG. 22A
FIG. 22B
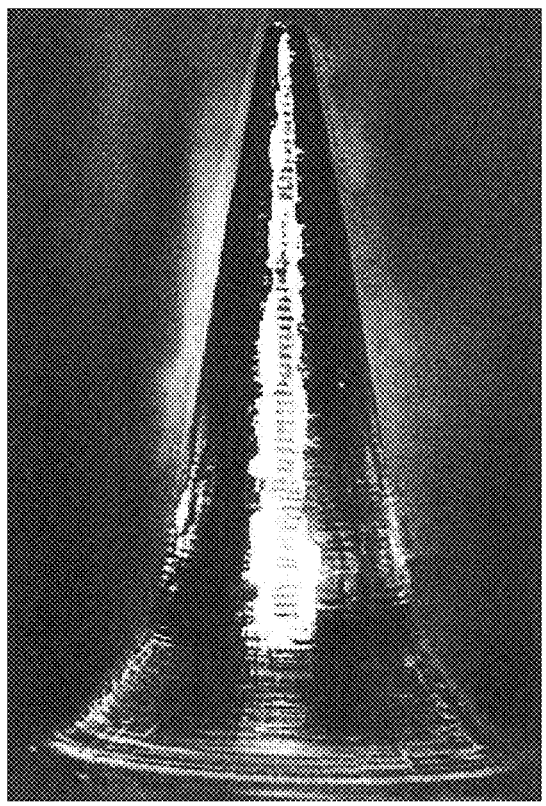
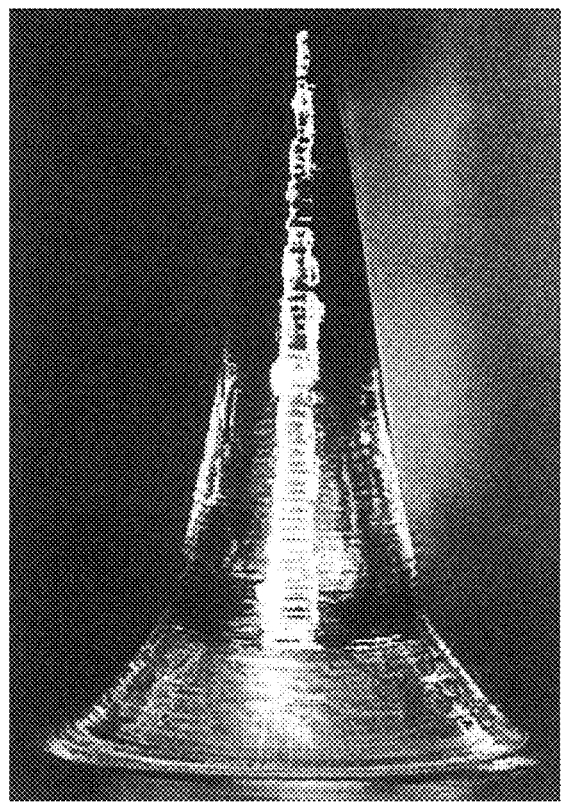

MICRONEEDLE ARRAY

CROSS-REFERENCE TO RELATED APPLICATIONS

This application is a Continuation of PCT International Application No. PCT/JP2017/014963 filed on Apr. 12, 2017, which claims priority under 35 U.S.C § 119(a) to Japanese Patent Application No. 2016-081778 filed on Apr. 15, 2016. Each of the above application(s) is hereby expressly incorporated by reference, in its entirety, into the present application.

BACKGROUND OF THE INVENTION

1. Field of the Invention

The present invention relates to a microneedle array containing a liposome.

2. Description of the Related Art

In recent years, a dissolution type microneedle array that contains a drug in a base material formed of a biosoluble substance has been developed. The microneedle array has a characteristic of less irritation to the nerve because needles are thin and short and is also referred to as "painless injection". For example, US2004/0087893A1 describes a dissolution type microneedle array as a system for performing controlled delivery of a drug to a patient. US2008/0269685A1 describes a microneedle array which includes a substrate and a plurality of needles. The microneedle array of US2008/0269685A1 includes a plurality of layers containing different polymers and one layer among these layers is included in a portion of a needle.

In the field of injections, the research and development utilizing a drug delivery system (DDS) that uses artificial fine particles have been promoted. Pharmacokinetic control and reduction of toxicity in the body can be realized by holding a drug in artificial fine particles. A liposome which is an artificial fine particle formed of a lipid bilayer is highly safe because a phospholipid to be used is a biological component, capable of easily adjusting the size and the lipid composition, and capable of enclosing various substances such as a water-soluble drug, a lipophilic drug, and a polymer. Therefore, the liposome has been attracting attention particularly as a carrier for a DDS pharmaceutical product.

International Journal of Pharmaceutics 447 (2013) p. 22 to 30, written by Lei Guo et al., discloses a microneedle array that contains a cationic liposome formed by enclosing ovalbumin. JP2015-521910A describes an applicator for applying a cosmetic to the human skin, including a base (a); a plurality of soluble microneedles (b) which are fixed to the base and protrude with a length long enough to enter the skin from the base, where, the microneedles are made of a material that can be disintegrated and dispersed in the skin; a cosmetic (c) which is delivered by the microneedles, for delivery into the skin by the microneedles; and a soluble external shell (d) which is configured of the soluble microneedles, in which one or more cosmetics are enclosed in the shell. JP2015-521910A describes that the cosmetic may be a soluble external shell which is substantially formed of a material selected from the group consisting of a hydrophobic material, a hydrophobically modified material, and a liposome.

SUMMARY OF THE INVENTION

International Journal of Pharmaceutics 447 (2013) p. 20 to 30, written by Lei Guo et al., describes a microneedle array containing a cationic liposome, but the cationic liposome is not preferable from the viewpoint of toxicity. JP2015-521910A describes microneedles containing a liposome, but research on the physical properties of the liposome has not been conducted yet.

In a case where a water-soluble polymer is mixed with liposomes, aggregation of liposomes may occur during the production of a microneedle array that contains liposomes. In a case where aggregation of liposomes occurs, a liquid containing the water-soluble polymer and the liposomes is unlikely to be sterilized and filtered. Therefore, the microneedle array is unlikely to be sterilized. Further, it is desirable that a drug is allowed to be localized at a tip of a needle at the time of producing a microneedle array using a liquid containing a drug.

An object of the present invention is to provide a microneedle array which is capable of suppressing aggregation of liposomes in a case where a water-soluble polymer is mixed with liposomes during production of the microneedle array and is capable of localizing a drug at a tip of a needle.

As a result of intensive research conducted by the present inventors in order to solve the above-described problems, it was found that a microneedle array that solves the above-described problems can be provided by using liposomes having a zeta potential of $-10$ mV or less, setting the content of a salt at a tip of a needle containing the liposomes to 2.5 mmol/g or less, or using a specific compound as an anionic compound constituting the liposomes, in the production of the microneedle array containing liposomes. The present invention has been completed based on these findings.

In other words, according to the present invention, the following inventions are provided.

[1] A microneedle array comprising: a sheet; and a plurality of needles which are present on an upper surface of the sheet, in which each needle contains a water-soluble polymer, a drug, a liposome, and a salt, a zeta potential of the liposome is $-10$ mV or less, the zeta potential is a zeta potential of a liquid obtained by diluting the liposome to 0.1 mg/mL with 10 mmol/L of a phosphoric acid aqueous solution having a pH of 7, and a content of the salt in a portion of each needle which contains the liposome is 2.5 mmol/g or less.

[2] The microneedle array according to [1], in which the liposome contains an anionic compound, and the anionic compound is at least one selected from the group consisting of phosphatidylglycerol, phosphatidylserine, phosphatidic acid, a lipid containing a polyoxyethylene chain, a surfactant, and a saponin.

[3] The microneedle array according to [1] or [2], in which the water-soluble polymer is electrically neutral.

[4] The microneedle array according to any one of [1] to [3], in which the water-soluble polymer is at least one selected from the group consisting of polyethylene glycol, polyvinylpyrrolidone, dextran, dextrin, hydroxyethyl starch, a cellulose derivative, and polyvinyl alcohol.

[5] The microneedle array according to any one of [1] to [4], in which the water-soluble polymer is hydroxyethyl starch, and the liposome contains phosphatidylcholine and distearoyl phosphatidylglycerol.

[6] A microneedle array comprising: a sheet; and a plurality of needles which are present on an upper surface of the sheet, in which each needle contains a water-soluble polymer, a drug, a liposome, and a salt, the liposome is a liposome which contains an anionic compound, and the anionic compound is at least one selected from the group consisting of phosphatidylglycerol, phosphatidylserine, phosphatidic acid, a lipid containing a polyoxyethylene chain, a surfactant, and a saponin.

[7] The microneedle array according to [6], in which the water-soluble polymer is electrically neutral.

[8] The microneedle array according to [6] or [7], in which the water-soluble polymer is at least one selected from the group consisting of polyethylene glycol, polyvinylpyrrolidone, dextran, dextrin, hydroxyethyl starch, a cellulose derivative, and polyvinyl alcohol.

[9] The microneedle array according to any one of [6] to [8], in which the water-soluble polymer is hydroxyethyl starch, and the liposome contains distearoyl phosphatidylglycerol.

[10] The microneedle array according to any one of [1] to [9], in which the drug is a hormone or a vaccine.

[11] The microneedle array according to any one of [1] to [10], in which the salt is a salt containing at least one selected from the group consisting of a sodium ion, a potassium ion, an ammonium ion, a lithium ion, and a silver ion.

According to the microneedle array of the present invention, it is possible to suppress aggregation of liposomes in a case where a water-soluble polymer is mixed with liposomes during production of the microneedle array. Further, according to the microneedle array of the present invention, it is possible to localize a drug at a tip of a needle.

BRIEF DESCRIPTION OF THE DRAWINGS

FIG. 22A shows the appearance of a microneedle array produced using the formulation of Comparative Example 7.

FIG. 22B shows the appearance of a microneedle array produced using the formulation of Example 1.

DESCRIPTION OF THE PREFERRED EMBODIMENTS

Figure 1A:
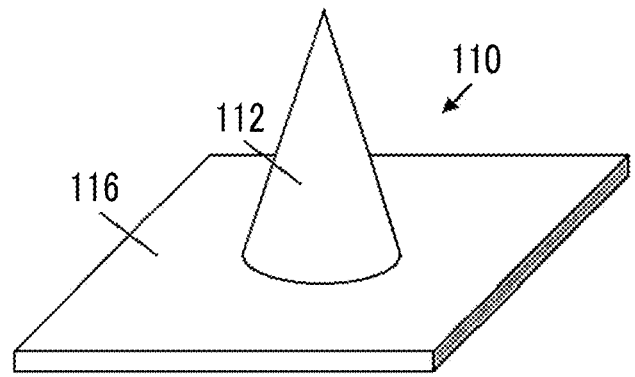
FIG. 1A is a perspective view illustrating a conical microneedle.

Hereinafter, embodiments of the present invention will be described in detail.

In the present specification, the expression "containing a predetermined amount of drug" means that a drug having an amount enough to exhibit drug efficacy is contained when the body surface is punctured. The expression "not containing a predetermined amount of drug" means that a drug having an amount enough to exhibit drug efficacy is not contained, and the range of the amount of the drug covers from a case where the drug is not contained at all to a case where the amount thereof is not enough to exhibit the drug efficacy.

Hereinafter, "containing a predetermined amount of drug" is expressed as "containing a drug" and "not containing a predetermined amount of drug" is expressed as "not containing a drug".

According to the present invention, aggregation of liposomes can be suppressed at the time of mixing a water-soluble polymer with liposomes and a liquid containing the water-soluble polymer and liposomes can be sterilized and filtered by using liposomes having a zeta potential of −10 mV or less, setting the content of a salt in a portion of a needle containing the liposomes to 2.5 mmol/g or less, or using a specific lipid as an anionic compound constituting the liposomes, in the production of the microneedle array. Further, with the above-described configuration of the present invention, the tip of a needle can be filled with a drug. The above-described effect of the present invention is an effect which cannot be expected at all from the past. Moreover, among liposomes, an anionic liposome whose surface is negatively charged is preferable from the viewpoints of pharmacokinetic control and reduction of toxicity in the body.

[Characteristics of Microneedle Array]

In the present invention, the zeta potential of a liquid obtained by diluting the liposome to 0.1 mg/mL with 10 mmol/L of a phosphoric acid aqueous solution (pH of 7) is −10 mV or less, preferably −12 mV or less, more preferably −15 mV or less, still more preferably −20 mV or less, and particularly preferably −30 mV or less. The zeta potential can be measured using a laser Doppler method (ELS-Z or the like (manufactured by Otsuka Electronics Co., Ltd.)). The lower limit of the zeta potential is not limited, and is typically approximately −100 mV.

In the microneedle array of the present invention, the content of a salt in a portion of a needle containing a liposome is 2.5 mmol/g or less, preferably 2.0 mmol/g or less, more preferably 1.2 mmol/g or less, still more preferably 0.8 mmol/g or less, and particularly preferably 0.6 mmol/g or less. The lower limit of the content of the salt is not particularly limited. The lower limit thereof may be 0 mmol/g, but is typically 0.01 mmol/g or greater.

Specific examples of the salt include a salt containing at least one selected from the group consisting of a sodium ion, a potassium ion, an ammonium ion, a lithium ion, and a silver ion. In a case where a plurality of kinds of salts are present, the total content of the salts is set to be in the above-described range.

The content of the salt in a portion of a needle containing a liposome can be measured in the following manner.

1. The tip of a needle is cut with a cutter and collected.
2. The needles collected in the item 1 are dissolved in water for injection.
3. The liquid obtained by dissolving the needles in the item 2 is measured using ion chromatography (DX-320 or the like (manufactured by Dionex Corporation)).

[Liposome]

A liposome is a closed vesicle formed of a lipid bilayer obtained by using a lipid and contains a water phase (inner water phase) in a space of the closed vesicle. The inner water phase contains water and the like. The liposome is typically present in a state of being dispersed in an aqueous solution (outer water phase) other than the closed vesicle. The liposome may be a single lamellar (also referred to as a single layer lamellar or a unilamellar, and a double layer membrane is a single structure) or a multilayer lamellar (also referred to as a multilamellar and has a structure of a plurality of double layer membranes in an onion shape, and the individual layers are partitioned by a watery layer). However, in the present invention, from the viewpoints of the safety and the stability for the medical applications, a liposome of a single lamellar is preferable.

The form of the liposome is not particularly limited. The liposome may encapsulate a drug. The "encapsulation" here indicates that the drug in the liposome is in the form of being contained in an inner water phase and the membrane itself. Examples of the form include a form in which a drug is enclosed in a closed space formed of a membrane and a form in which a drug is encapsulated in the membrane itself, and a combination of these may be employed.

The average particle diameter of the liposomes is preferably in a range of 10 nm to 150 nm, more preferably in a range of 20 nm to 110 nm, and still more preferably in a range of 30 nm to 90 nm.

It is preferable that the liposomes have a spherical shape or are in the form similar to the spherical shape.

The average particle diameter of the liposomes can be measured using a dynamic light scattering method (ELS-Z2 or the like (manufactured by Otsuka Electronics Co., Ltd.)).

The component constituting the lipid bilayer of liposomes is selected from the lipid and the anionic compound. As the lipid, a component which is dissolved in a mixed solvent of a water-soluble organic solvent and an ester-based organic solvent can be optionally used. Examples of the lipid include a phospholipid, a lipid other than the phospholipid, cholesterols, a lysophospholipid, and derivatives thereof. These components may be configured of a single component or a plurality of kinds of components.

Examples of the phospholipid include natural or synthetic phospholipids such as phosphatidylcholine (lecithin), phosphatidylglycerol, phosphatidic acid, phosphatidylethanolamine, phosphatidylserine, phosphatidylinositol, sphingomyelin, and cardiolipin, and those hydrogenated to these (hydrogenated soy phosphatidylcholine (HSPC)). Among these, hydrogenated phospholipids such as hydrogenated soy phosphatidylcholine and sphingomyelin are preferable, and hydrogenated soy phosphatidylcholine is more preferable. Further, in the present invention, the "phospholipid" also includes a phospholipid derivative obtained by modifying a phospholipid.

Examples of the lipid other than the phospholipid include lipids that do not contain phosphoric acid, and specific examples thereof include a glycerolipid which does not have a phosphoric acid moiety in the molecule thereof and a sphingolipid which does not have a phosphoric acid moiety in the molecule thereof. Further, in the present invention, the "lipid other than the phospholipid" also includes a derivative of the lipid other than the phospholipid obtained by modifying the lipid other than the phospholipid.

In the present invention, it is preferable that the liposome contains at least a certain amount of the anionic compound as a constituent component. Since it is speculated that the electric charge intensity of the negative electric charge depends on the proportion of the anionic compound in the constituent component of the liposome, it is preferable that the content of the anionic compound in the liposome is high. Specifically, the content of the anionic compound is preferably 2 mol % or greater, more preferably 3 mol % or greater, and particularly preferably 5 mol % or greater with respect to the mol number of the total amount of the compounds constituting the lipid bilayer of the liposome. The upper limit of the content of the anionic compound is not particularly limited, but is typically approximately 50 mol %.

The electric charge intensity of the negative electric charge depends on the kind of the anionic compound in some cases. The anionic compound is not limited as long as electric charges are charged on the compound, and examples thereof include phosphatidylglycerol, phosphatidylserine, phosphatidic acid, a lipid containing a polyoxyethylene chain, a surfactant, and a saponin.

Examples of the cholesterols include cholesterol which has cyclopentahydrophenanthrene as a basic skeleton and in which some or all carbon atoms are hydrogenated and derivatives thereof. As an example, cholesterol is exemplified. The curvature of a lipid membrane is increased as the average particle diameter is decreased to 100 nm or less. Since the distortion of membranes arranged in the liposome is increased, a water-soluble drug is more likely to be leaked. As a means of suppressing the leakiness, it is effective to add cholesterol or the like for the purposes of filling the gap formed by the distortion of the membranes due to the lipid (membrane stabilizing effect).

It is expected to reduce the fluidity of the liposome membranes by filling the gap between liposome membranes through addition of cholesterols to the liposome. Typically, it is desirable that the liposome contains cholesterol such that the amount of cholesterols therein does not exceed approximately 50 mol % with respect to the mol number of the total amount (total lipids) of the lipid components.

The content of the cholesterols is preferably in a range of 10 mol % to 35 mol %, more preferably in a range of 15 mol % to 25 mol %, and still more preferably in a range of 17 mol % to 21 mol % with respect to the total amount of the lipids constituting the liposome.

(Method of Producing Liposomes)

A method of producing liposomes is not particularly limited. The liposomes can be produced by, for example, emulsifying the lipid dissolved in an organic solvent.

In an emulsification step, the lipid can be emulsified by mixing a water phase with an oil phase obtained by dissolving at least one lipid in an organic solvent and stirring the aqueous solution containing the lipid. By mixing the water phase with the oil phase obtained by dissolving the lipid in an organic solvent and stirring the aqueous solution, an emulsified liquid obtained by emulsifying the oil phase and the water phase in an oil in water type (O/W type) is prepared. After the oil phase is mixed with the water phase, liposomes are formed by performing an evaporation step to remove a part or all of the organic solvent derived from the oil phase. Alternatively, liposomes are formed by evaporating a part or all of the organic solvent in the oil phase in the process of the stirring and the emulsification.

As the stirring method, ultrasonic waves or mechanical shear force is used for micronizing particles. Further, in order to make the particle diameter uniform, an extruder treatment of passing the particles through a filter having a constant pore diameter or a microfluidizer treatment can be performed. In a case where an extruder or the like is used, univesicular liposomes can be obtained by dividing multivesicular liposomes which have been secondarily formed. From the viewpoint of simplifying the production step, it is preferable that empty liposomes are used for the next step without performing an extrusion treatment thereon.

The emulsification step is not particularly limited, but it is preferable that the emulsification step is a step of micronizing particles by applying high shearing and emulsifying the organic solvent. As necessary, liposomes can be formed by evaporating (desolventizing) the organic solvent used in the emulsification step.

The liquid temperature of the emulsification step during the production of liposomes can be appropriately adjusted, but it is preferable that the liquid temperature thereof is set to be higher than or equal to the phase transition temperature of the lipid using the liquid temperature at the time of mixing the oil phase with the water phase. For example, in a case where a lipid having a phase transition temperature of 35° C. to 40° C. is used, the liquid temperature thereof is preferably in a range of 35° C. to 70° C.

The organic solvent used as the oil phase is not particularly limited, and an alcohol, an ester, chloroform, methylene chloride, hexane, cyclohexane, or the like can be used as the organic solvent.

The alcohol used in the present invention is not particularly limited, but it is preferable to use an alcohol having 1 to 6 carbon atoms. Specific examples thereof include methanol, ethanol, 1-propanol, 2-propanol, 1-butanol, 2-butanol, and 3-methyl-1-butanol. As the alcohol used in the present invention, it is more preferable to use ethanol from the viewpoint of the polarity.

The ester used in the present invention is not particularly limited, but it is preferable to use ester acetate. Specific examples thereof include methyl acetate, ethyl acetate, propyl acetate, isopropyl acetate, butyl acetate, and isobutyl acetate. As the ester used in the present invention, it is more preferable to use ethyl acetate from the viewpoint of the polarity or the lipophilicity.

(Water Phase)

The water phase indicates an outer water phase and an inner water phase.

The outer water phase indicates an aqueous solution that disperses liposomes. For example, in a case of an injection, a solution that occupies outside the liposomes of a dispersion liquid containing liposomes stored by being packed in a vial bottle or a prefilled syringe becomes the outer water phase. Further, similar to an attached dispersion liquid or a liquid that disperses liposomes at the time of administration due to a dissolution solution other than the attached dispersion liquid, a solution that occupies outside the liposomes of a dispersion liquid containing liposomes becomes an outer water phase.

The inner water phase indicates a water phase in a closed vesicle separated from the lipid bilayer membrane of a liposome.

As the aqueous solution (outer water phase) that disperses liposomes, water (distilled water, water for injection, or the like), physiological saline, various buffer solutions, an aqueous solution containing saccharides, or a mixture (aqueous solvent) of these is preferably used during the production of liposomes. The buffer solution is not limited to an organic buffer solution or an inorganic buffer solution, but a buffer solution having a buffer action around the hydrogen ion concentration close to the body fluid is suitably used, and examples thereof include a phosphate buffer solution, a tris buffer solution, a citrate buffer solution, an acetate buffer solution, and a Good's buffer. The pH of the water phase can be set to be in a range of, for example, 5 to 9 and preferably in a range of 7 to 8. It is preferable to use a phosphate buffer solution (for example, with a pH of 7.4) as the aqueous solution (outer water phase) that disperses liposomes. The inner water phase of liposomes may be an aqueous solution that disperses liposomes during the production of liposomes or water, physiological saline, various buffer solutions, an aqueous solution containing saccharides, or a mixture of these, to be newly added. It is preferable that water used as the outer water phase or the inner water phase does not contain impurities (dust, chemical substances, and the like).

The physiological saline indicates an inorganic salt solution adjusted to be isotonic with the human body and may further have a buffer function. Examples of the physiological saline include saline that contains 0.9 w/v % (weight/volume %) of sodium chloride, phosphate buffered saline (hereinafter, also referred to as PBS), and tris buffered saline.

The aqueous solution containing liposomes prepared by performing the emulsification step may be subjected to a post-treatment according to a method of centrifugation, ultrafiltration, dialysis, gel filtration, or freeze drying in order to remove components which have not been contained in the liposomes or to adjust the concentration or the osmotic pressure.

(Extrusion Treatment)

In the obtained liposomes, the particle diameter can be made uniform using dialysis, a filtration method, or an extrusion treatment.

The extrusion treatment indicates a step of applying physical shearing to micronize particles by passing the liposomes through a filter having pores. The particles can be rapidly micronized by keeping the temperature of the liposome dispersion liquid and the filter to a temperature higher than or equal to the phase transition temperature of the membranes constituting the liposomes at the time of passing the liposomes through the filter.

It is preferable that the liposomes are sterilized and filtered. As a filtration method, unnecessary substances can be removed from the aqueous solution containing the liposomes using a hollow fiber membrane, a reverse osmosis membrane, a membrane filter, or the like. It is preferable that the liposomes are filtered using a filter having a pore diameter (preferably a filtration sterilization filter having a diameter of 0.2 μm) that enables sterilization.

[Configuration of Microneedle Array]

The microneedle array of the present invention is a microneedle array including a sheet; and a plurality of needles present on an upper surface of the sheet.

In the present invention, plural means one or more.

The microneedle array of the present invention includes at least a sheet or needles and a drug is carried and supported in the needles in order to efficiently administer the drug into the skin.

The microneedle array of the present invention is a device in which a plurality of needles are arranged in an array on the upper surface side of the sheet. The needles may be directly arranged on the upper surface of the sheet or may be arranged on the upper surfaces of frustums arranged on the upper surface of the sheet.

The sheet is a foundation for supporting needles and has a planar shape as the shape of the sheet 116 illustrated in FIGS. 1 to 8. At this time, the upper surface of the sheet indicates the surface on which the plurality of needles are arranged in an array.

The area of the sheet is not particularly limited, but is preferably in a range of 0.005 to 1000 $mm^2$, more preferably in a range of 0.05 to 500 $mm^2$, and still more preferably in a range of 0.1 to 400 $mm^2$.

The thickness of the sheet is a distance between the surface in contact with frustums or needles and the surface on the opposite side. The thickness of the sheet is preferably in a range of 1 μm to 2000 μm, more preferably in a range of 3 μm to 1500 μm, and still more preferably in a range of 5 μm to 1000 μm.

The sheet contains a water-soluble polymer. The sheet may be formed of a water-soluble polymer or may contain other additives (for example, disaccharides). Further, it is preferable that the sheet does not contain a drug.

The water-soluble polymer contained in the sheet is not particularly limited, and examples thereof include polysaccharides, polyvinylpyrrolidone, polyoxyethylene polyoxypropylene glycol, polyethylene glycol, polyvinyl alcohol, and protein (for example, gelatin). Examples of the polysaccharides include hyaluronic acid, sodium hyaluronate, pullulan, dextran, dextrin, sodium chondroitin sulfate, a cellulose derivative (for example, a water-soluble cellulose derivative obtained by partially modifying cellulose such as carboxymethyl cellulose, hydroxypropyl cellulose, or hydroxypropyl methylcellulose), hydroxyethyl starch, and gum Arabic. The above-described components may be used alone or in mixture of two or more kinds thereof.

Among these, hydroxyethyl starch, hydroxypropyl cellulose, hydroxypropyl methyl cellulose, pullulan, dextran, sodium chondroitin sulfate, sodium hyaluronate, carboxymethyl cellulose, polyvinylpyrrolidone, polyoxyethylene polyoxypropylene glycol, polyethylene glycol, and polyvinyl alcohol are more preferable; and dextran is particularly preferable.

Disaccharides may be added to the sheet and examples of the disaccharides include sucrose, lactulose, lactose, maltose, trehalose, and cellobiose. Among these, sucrose, maltose, and trehalose are particularly preferable.

The microneedle array is configured of a plurality of needles arranged in an array on the upper surface of the sheet. The needles have a projected structure with a tip, and the shape thereof is not limited to a needle shape having a sharp tip and may be a shape with a blunt tip.

Examples of the shape of a needle include a conical shape, a polygonal pyramid shape (square pyramid shape or the like), and a spindle shape. For example, a needle may have a shape of the needle 112 illustrated in any of FIGS. 1 to 8, in which the entire shape of the needle may be a conical shape, a polygonal pyramid shape (square pyramid shape or the like), or a shape of a structure in which the inclination (angle) of the side surface of the needle is continuously changed. Further, a needle may have a multilayer structure with two or more layers, in which the inclination (angle) of the side surface of the needle is discontinuously changed.

In a case where the microneedle array of the present invention is applied to the skin, it is preferable that the needles are inserted into the skin and the upper surface or a part of the sheet is brought into contact with the skin.

The height (length) of a needle indicates the length of a perpendicular line drawn from the tip of the needle to a frustum or the sheet (in a case where a frustum is not present). The height (length) of a needle is not particularly limited, but is preferably in a range of 50 μm to 3000 μm, more preferably in a range of 100 μm to 1500 μm, and still more preferably in a range of 100 μm to 1000 μm. It is preferable that the length of a needle is 50 μm or greater because a drug can be percutaneously administered. Further, it is preferable that the length of a needle is 3000 μm or less because occurrence of pain resulting from the contact of needles with the nerve is prevented and bleeding can be avoided.

The interface between a frustum (or a needle in a case where a frustum is not present) and the sheet is referred to as a base. The distance between a base of one needle and a point farthest from the base is preferably in a range of 50 μm to 2000 μm, more preferably in a range of 100 μm to 1500 μm, and still more preferably in a range of 200 μm to 1000 μm.

The number of needles to be arranged in one microneedle is preferably in a range of 1 to 2000, more preferably in a range of 3 to 1000, and still more preferably in a range of 5 to 500. In a case where one microneedle array includes two needles, the interval between needles indicates the distance between feet of each perpendicular line drawn from the tip of a needle to a frustum or the sheet (in the case where a frustum is not present). In a case where one microneedle array includes three or more needles, the interval between needles to be arranged indicates an average value obtained by acquiring the distance between a foot of a perpendicular line drawn from the tip of a needle to a frustum or the sheet (in the case where frustums are not present) and a foot of a perpendicular line drawn from the tip of a needle closest to the needle to a frustum or the sheet and averaging the values obtained from all needles. The interval between needles is preferably in a range of 0.1 mm to 10 mm, more preferably in a range of 0.2 mm to 5 mm, and still more preferably in a range of 0.3 mm to 3 mm.

The needles contain a water-soluble polymer, a drug, a liposome, and a salt.

It is preferable that the water-soluble polymer is a biosoluble substance such that a human body is not damaged even when needles remain in the skin.

The water-soluble polymer contained in the needles is not particularly limited, and examples thereof include polysaccharides, polyvinylpyrrolidone, polyoxyethylene polyoxypropylene glycol, polyethylene glycol, polyvinyl alcohol, and protein (for example, gelatin). Examples of the polysaccharides include hyaluronic acid, sodium hyaluronate, pullulan, dextran, dextrin, sodium chondroitin sulfate, a cellulose derivative (for example, a water-soluble cellulose derivative obtained by partially modifying cellulose such as carboxymethyl cellulose, hydroxypropyl cellulose, or hydroxypropyl methylcellulose), hydroxyethyl starch, and gum Arabic. The above-described components may be used alone or in mixture of two or more kinds thereof.

Among these, at least one selected from the group consisting of polyethylene glycol, polyvinylpyrrolidone, dextran, dextrin, hydroxyethyl starch, a cellulose derivative, and polyvinyl alcohol is preferable and hydroxyethyl starch is particularly preferable. Further, an electrically neutral water-soluble polymer is preferable because aggregation is unlikely to occur at the time of being mixed with a drug. The electrically neutral water-soluble polymer indicates a water-soluble polymer that does not have electric charges and, more specifically, a water-soluble polymer that does not contain a group having electric charges. The water-soluble polymer contained in the needles may be the same as or different from the water-soluble polymer contained in the sheet.

Disaccharides may be added to the needles (particularly, the needle tip region) and examples of the disaccharides include sucrose, lactulose, lactose, maltose, trehalose, and cellobiose. Among these, sucrose, maltose, and trehalose are preferable.

The drug indicates a substance that affects a human body. It is preferable that the drug is selected from peptides (including peptide hormones or the like) or derivatives thereof, proteins, a nucleic acid, polysaccharides, vaccines, adjuvants, a pharmaceutical compound belonging to a water-soluble low molecular compound, or cosmetic ingredients. The molecular weight of the drug is not particularly limited, but a drug having a molecular weight of 500 or greater is preferable in a case of proteins.

Examples of peptides or derivatives thereof and proteins include calcitonin, adrenocorticotropic hormone, parathyroid hormone (PTH), human PTH (1→34), insulin, exendin, secretin, oxytocin, angiotensin, β-endorphin, glucagon, vasopressin, somatostatin, gastrin, luteinizing hormone releasing hormone, enkephalin, neurotensin, atrial natriuretic peptide, growth hormone, growth hormone releasing hormone, bradykinin, substance P, dynorphin, thyroid stimulating hormone, prolactin, interferon, interleukin, granulocyte colony stimulating factor (G-CSF), glutathione peroxidase, superoxide dismutase, desmopressin, somatomedin, endothelin, and salts of these.

Examples of the vaccines include influenza antigen (influenza vaccine), hepatitis B virus surface antigen (HBs) antigen, hepatitis Be antigen (HBe antigen), Bacille de calmette et Guerin (BCG) antigen, measles antigen, rubella antigen, varicella antigen, yellow fever antigen, shingles antigen, rotavirus antigen, influenza bacilli b type (Hib) antigen, rabies antigen, cholera antigen, diphtheria antigen, pertussis antigen, tetanus antigen, inactivated polio antigen, Japanese encephalitis antigen, human papilloma antigen, and antigens obtained by mixing two to four types of these.

Examples of the adjuvants include aluminum salts such as aluminum phosphate, aluminum chloride, and aluminum hydroxide, emulsions such as MF59 (registered trademark) and AS03 (Adjuvant System 03), liposomes, plant-derived components, a nucleic acid, biopolymers, cytokine, peptides, proteins, and sugar chains.

Among these, as the drug, at least one selected from the group consisting of peptide hormones, vaccines, and adjuvants is preferable. Growth hormone is particularly preferable as peptide hormones and influenza vaccine is particularly preferable as vaccines.

The content of the drug in all needles is not particularly limited, but is preferably in a range of 1 to 60% by mass, more preferably in a range of 1 to 50% by mass, and particularly preferably in a range of 1 to 45% by mass with respect to the mass of the solid content of needles.

Hereinafter, preferred embodiments of the present invention will be described with reference to the accompanying drawings, but the present invention is not limited thereto.

FIGS. 1 to 8 are partially enlarged views illustrating a microneedle 110 in the microneedle array. The microneedle array of the present invention is configured by the plurality of needles 112 being formed on the surface of the sheet 116 (in the figured, one needle 112 is shown on the sheet 116 or one frustum 113 and one needle 112 are shown on the sheet 116 and this is referred to as the microneedle 110).

Figure 1B:
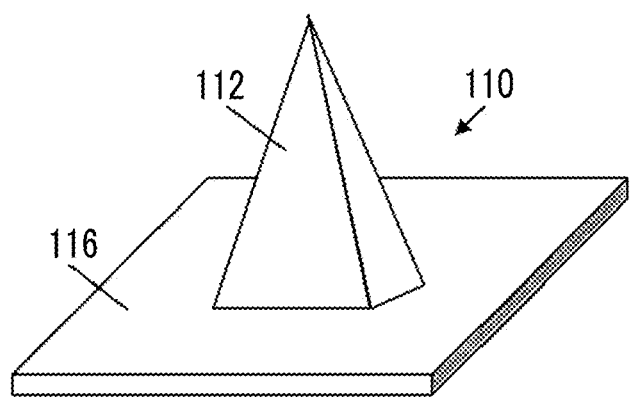
FIG. 1B is a perspective view illustrating a pyramid-like microneedle.
Figure 1C:
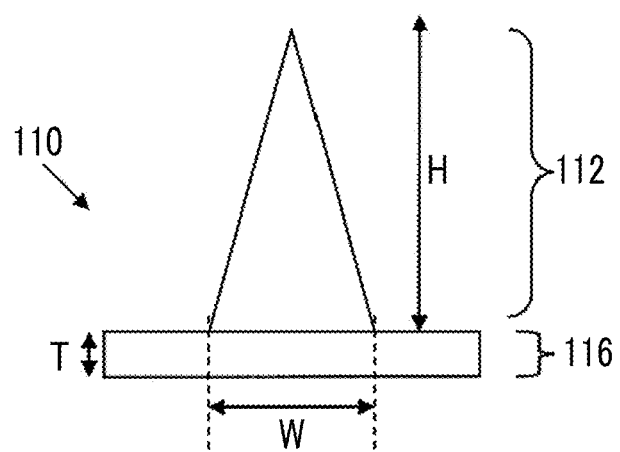
FIG. 1C is a cross-sectional view illustrating a conical and pyramid-like microneedle.

The needle 112 has a conical shape in FIG. 1A and the needle 112 has a square pyramid shape in FIG. 1B. In FIG. 1C, H represents the height of the needle 112, W represents the diameter (width) of the needle 112, and T represents the height (thickness) of the sheet 116.

Figure 2:
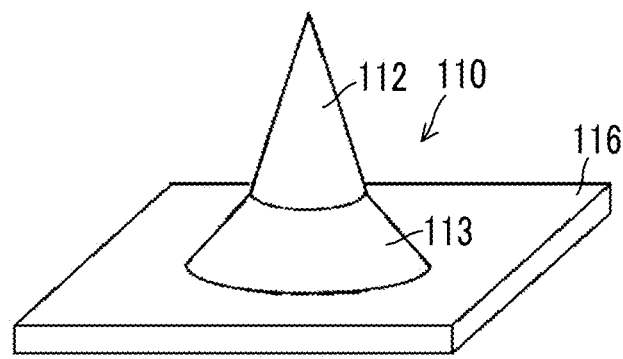
FIG. 2 is a perspective view illustrating a microneedle in another shape.
Figure 3:
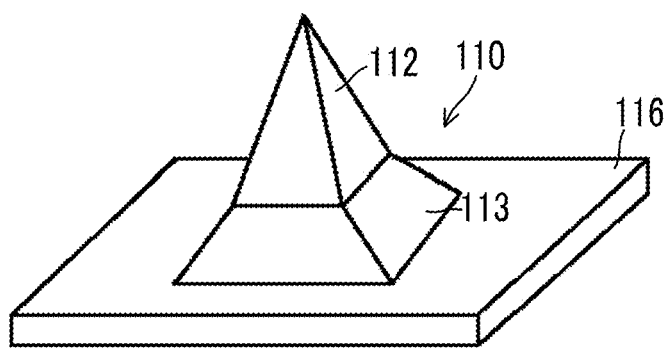
FIG. 3 is a perspective view illustrating a microneedle in another shape.

FIGS. 2 and 3 illustrate microneedles 110, on which the frustum 113 and the needle 112 are formed and which have different shapes, formed on the surface of the sheet 116. In FIG. 2, the frustum 113 has a truncated conical shape and the needle 112 has a conical shape. In FIG. 3, the frustum 113 has a truncated square pyramid shape and the needle 112 has a square pyramid shape. However, the shape of the needle is not particularly limited.

Figure 4:
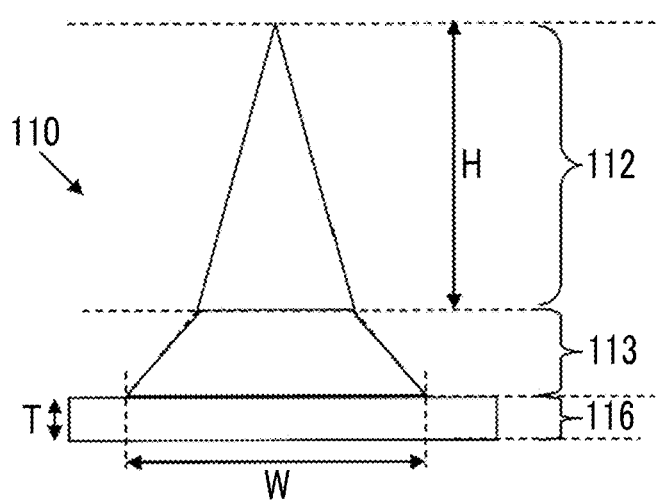
FIG. 4 is a cross-sectional view of the microneedles illustrated in FIGS. 2 and 3.

FIG. 4 is a cross-sectional view illustrating the microneedles 110 illustrated in FIGS. 2 and 3. In FIG. 4, H represents the height of the needle 112, W represents the diameter (width) of the base, and T represents the height (thickness) of the sheet 116.

It is preferable that the microneedle array of the present invention has a shape of the microneedle 110 of FIG. 4 other than the shape of the microneedle 110 in FIG. 1C. With such a configuration, the volume of all needles becomes larger so that a greater amount of drug can be concentrated on the tip of a needle when the microneedle array is produced.

Figure 5:
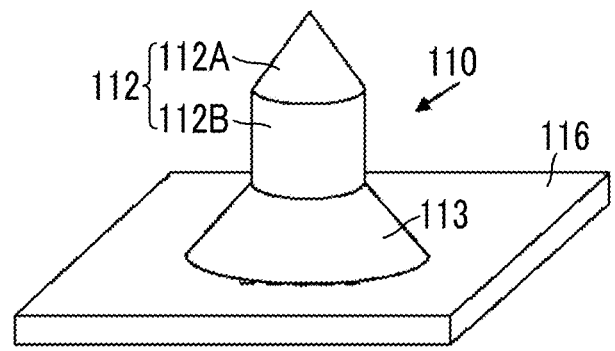
FIG. 5 is a perspective view illustrating a microneedle in another shape.
Figure 6:
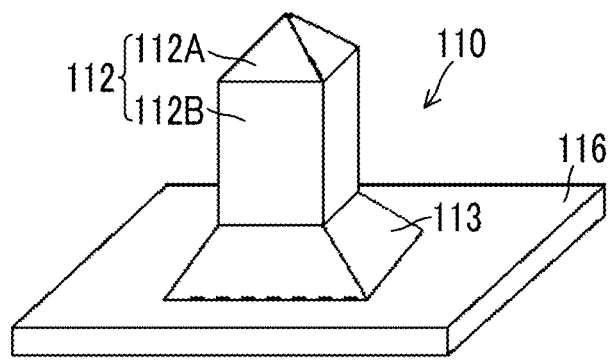
FIG. 6 is a perspective view illustrating a microneedle in another shape.

FIGS. 5 and 6 illustrate microneedles 110 in different shapes.

A first layer 112A of the needle illustrated in FIG. 5 has a conical shape and a second layer 112B of the needle in FIG. 6 has a columnar shape. The first layer 112A of the needle illustrated in FIG. 6 has a square pyramid shape and the second layer 112B has a square columnar shape. However, the shape of a needle is not limited to these shapes.

Figure 7:
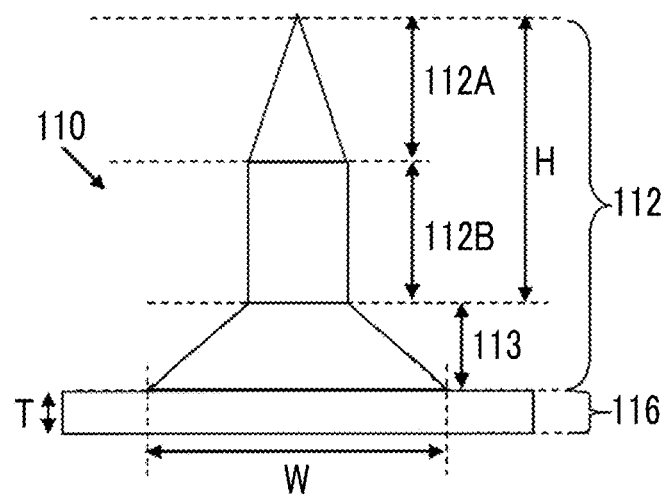
FIG. 7 is a cross-sectional view of the microneedles illustrated in FIGS. 5 and 6.

FIG. 7 is a cross-sectional view illustrating the microneedles 110 illustrated in FIGS. 5 and 6. In FIG. 7, H represents the height of the needle 112, W represents the diameter (width) of the base, and T represents the height (thickness) of the sheet 116.

Figure 8:
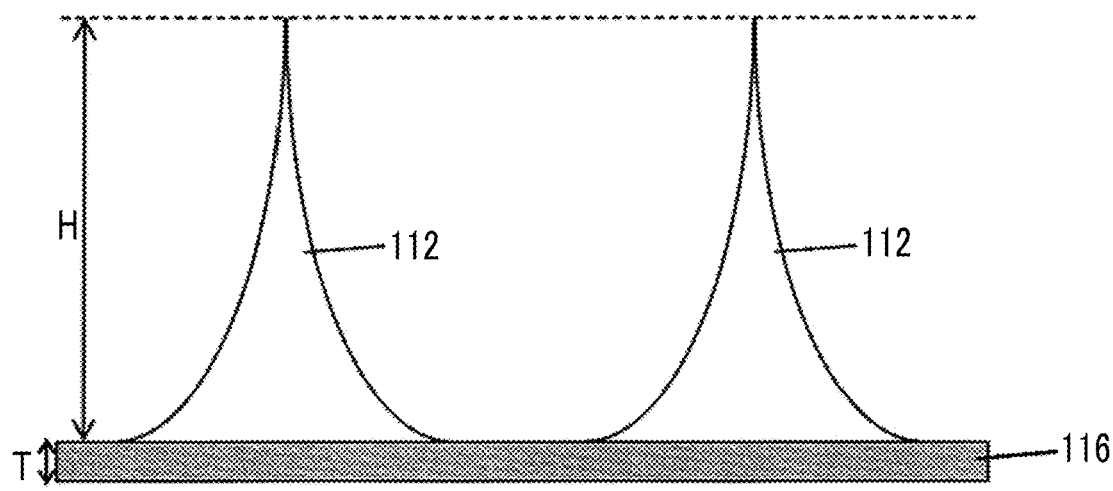
FIG. 8 is a cross-sectional view of a microneedle in another shape in which the inclination (angle) of a side surface of a needle is continuously changed.

FIG. 8 is a cross-sectional view of a microneedle in another shape in which the inclination (angle) of the side surface of the needle 112 is continuously changed. In FIG. 8, H represents the height of the needle 112 and T represents the height (thickness) of the sheet 116.

In the microneedle array of the present invention, it is preferable that needles are arranged at intervals of approximately 0.1 to 10 needles per 1 mm in a row. It is more preferable that the microneedle array has 1 to 10000 microneedles per 1 cm$^2$. When the density of microneedles is set to 1 needle/cm$^2$ or greater, the microneedles can efficiently puncture the skin. When the density of the microneedles is set to 10000 needles/cm$^2$ or less, the microneedle array can sufficiently puncture the skin. The density of needles is preferably in a range of 10 to 5000 needles/cm$^2$, more preferably in a range of 25 to 1000 needles/cm$^2$, and particularly preferably in a range of 25 to 400 needles/cm$^2$.

The microneedle array of the present invention can be supplied in a sealed storage form together with a drying agent. As the drying agent, known drying agents (such as silica gel, calcined lime, calcium chloride, silica alumina, and a sheet-like drying agent) can be used.

[Method of Producing Microneedle Array]

The microneedle array of the present invention can be produced by the following method in conformity with the method described in, for example, JP2013-153866A or WO2014/077242A.

(Preparation of Mold)

Figure 9A:
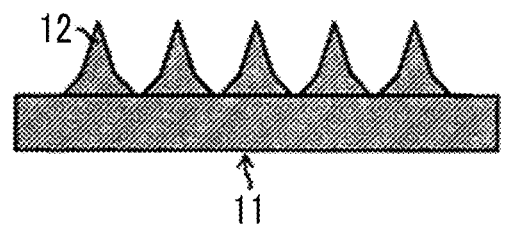
FIGS. 9A to 9C are step views illustrating a method of producing a mold.
Figure 9B:
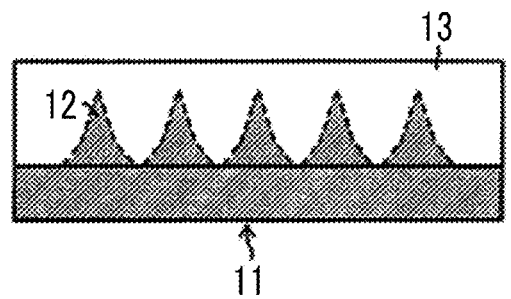
Figure 9C:
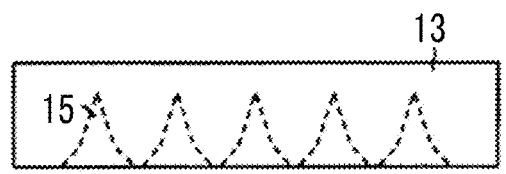

FIGS. 9A to 9C are step views illustrating a method of preparing a mold (die). As illustrated in FIG. 9A, first, an original plate is prepared used to prepare the mold. There are two methods for preparing an original plate 11.

According to the first method, a Si substrate is coated with a photoresist, exposed, and then developed. Further, an array of shaped portions 12 having a conical shape (projection) is prepared on the surface of the original plate 11 by performing etching using reactive ion etching (RIE) or the like. In addition, when the etching such as RIE or the like is performed so as to form shaped portions having a conical shape on the surface of the original plate 11, the portions having a conical shape can be formed by performing etching in an oblique direction while the Si substrate rotates. According to the second method, an array of the shaped portions 12 having a square pyramid shape or the like is formed on the surface of the original plate 11 by performing processing on a metal substrate such as Ni using a cutting tool such as a diamond bit.

Next, a mold is prepared. Specifically, a mold 13 is prepared using the original plate 11 as illustrated in FIG. 9B. As the method of preparing the mold, four methods are considered.

According to the first method, a silicone resin obtained by adding a curing agent to polydimethylsiloxane (PDMS, for example, SYLGARD 184 (registered trademark, manufactured by Dow Corning Toray Co., Ltd.)) is poured into the original plate 11, subjected to a heat treatment at 100° C., cured, and peeled from the original plate 11. According to the second method, an ultraviolet (UV) cured resin which is cured by being irradiated with ultraviolet rays is poured into the original plate 11, irradiated with ultraviolet rays in a nitrogen atmosphere, and peeled off from the original plate 11. According to the third method, a solution obtained by dissolving a plastic resin such as polystyrene or polymethyl methacrylate (PMMA) in an organic solvent is poured into the original plate 11 coated with a peeling agent, dried so that the organic solvent is volatilized, and cured, and then peeled off from the original plate 11. According to the fourth method, an inverted product is produced using Ni electroforming.

In this manner, the mold 13 formed by needle-like recesses 15, which have an inverted shape of the conical shape or the pyramid shape of the original plate 11, being two-dimensionally arranged is prepared. The mold 13 prepared in the above-described manner is illustrated in FIG. 9C.

Figure 10:
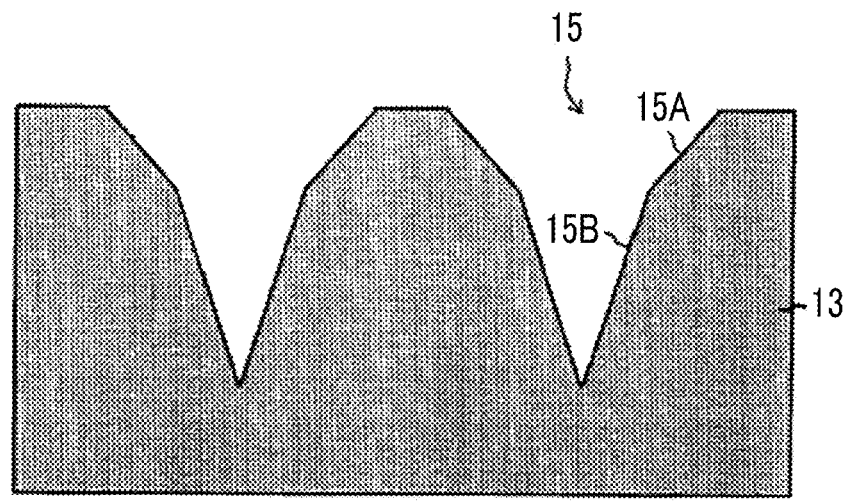
FIG. 10 is an enlarged view of a mold.

FIG. 10 illustrates another preferred embodiment of the mold 13. The needle-like recess 15 includes a tapered inlet portion 15A which becomes narrower in a depth direction from the surface of the mold 13 and a tip recess 15B which becomes tapered in the depth direction. When the inlet portion 15A has a tapered shape, the needle-like recess 15 is easily filled with the water-soluble polymer-dissolved solution.

Figure 11:
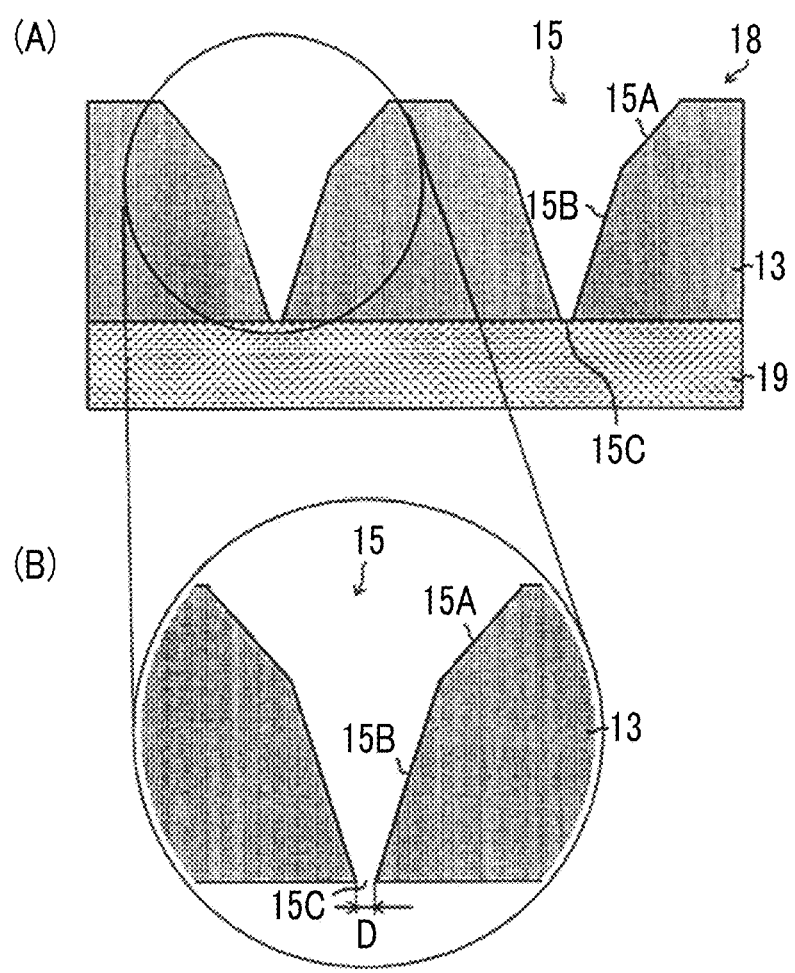
FIG. 11 is a cross-sectional view illustrating a mold in another shape.

FIG. 11 illustrates a more preferred embodiment of a mold complex 18 at the time of producing the microneedle array. The (A) portion of FIG. 11 illustrates the mold complex 18. The (B) portion of FIG. 11 is a partially enlarged view of a portion enclosed by a circle in the (A) portion.

As illustrated in the (A) portion of FIG. 11, the mold complex 18 includes the mold 13 having an air vent hole 15C formed on the tip (bottom) of the needle-like recess 15; and an air permeating sheet 19 which is bonded to the rear surface of the mold 13 and is formed of a material that permeates a gas and does not permeate a liquid. The air vent hole 15C is formed as a through-hole penetrating the rear surface of the mold 13. Here, the rear surface of the mold 13 indicates the surface on a side on which the air vent hole 15C is formed. With this configuration, the tip of the needle-like recess 15 communicates with the air through the air vent hole 15C and the air permeating sheet 19.

When such a mold complex 18 is used, only the air present in the needle-like recess 15 can be released from the needle-like recess 15 without permeation of the polymer-dissolved solution filling the needle-like recess 15. In this manner, the property of transferring the shape of the needle-like recess 15 to a polymer becomes excellent in the above-described manner and a sharper needle can be formed.

A diameter D (diameter) of the air vent hole 15C is preferably in a range of 1 to 50 µm. In a case where the diameter D of the air vent hole 15C is less than 1 µm, the air vent hole 15C cannot be sufficiently used as an air bend hole. Further, in a case where the diameter D of the air vent hole 15C is greater than 50 µm, the sharpness of the tip of a formed microneedle is damaged.

As the air permeating sheet 19 formed of a material that permeates a gas and does not permeate a liquid, for example, an air permeating film (Poreflon (registered trademark), FP-010, manufactured by Sumitomo Electric Industries, Ltd.) can be suitably used.

As the material used for the mold 13, an elastic material or a metal material can be used. Among these, an elastic material is preferable and a material having a high gas permeability is more preferable. The oxygen permeability, which is a representative example of the gas permeability, is preferably $1 \times 10^{-12}$ (mL/s·m$^2$·Pa) or greater and more preferably $1 \times 10^{-10}$ (mL/s·m$^2$·Pa) or greater. Further, 1 mL is $10^{-6}$ m$^3$. When the gas permeability is in the above-described range, the air present in a recess of the mold 13 can be released from the die and a microneedle array with less defects can be produced. Specific examples of such materials include materials obtained by melting or dissolving, in a solvent, a silicone resin (for example, SYLGARD 184 (registered trademark, manufactured by Dow Corning Toray Co., Ltd.) or KE-1310ST (product number, manufactured by Shin-Etsu chemical Co., Ltd.)), a UV curable resin, or a plastic resin (for example, polystyrene or polymethyl methacrylate (PMMA)). Among these, a silicone rubber-based material is preferable since the material has durability to transfer resulting from repetitive pressure and has excellent peeling properties with respect to a material. Further, examples of the metal material include Ni, Cu, Cr, Mo, W, Ir, Tr, Fe, Co, MgO, Ti, Zr, Hf, V, Nb, Ta, α-aluminum oxide, zirconium oxide, stainless (for example, STAVAX (registered trademark) of Bohler-Uddeholm KK), and alloys thereof. As the material of a frame 14, the same material as the material of the mold 13 can be used.

(Water-Soluble Polymer-Dissolved Solution)

In the present invention, it is preferable to prepare a water-soluble polymer-dissolved solution containing a drug, a liposome, and a salt used to form at least a part of a needle and a water-soluble polymer-dissolved solution used to form the sheet.

The type of water-soluble polymer is as described in the present specification above.

The concentration of the water-soluble polymer in any of the water-soluble polymer-dissolved solutions varies depending on the type of the water-soluble polymer to be used, and is preferably in a range of 1 to 50% by mass. Further, a solvent used for dissolution may be a solvent other than water (hot water) as long as the solvent has volatility, and methyl ethyl ketone (MEK) or an alcohol can be used as the solvent.

(Formation of Needle)

Figure 12A:
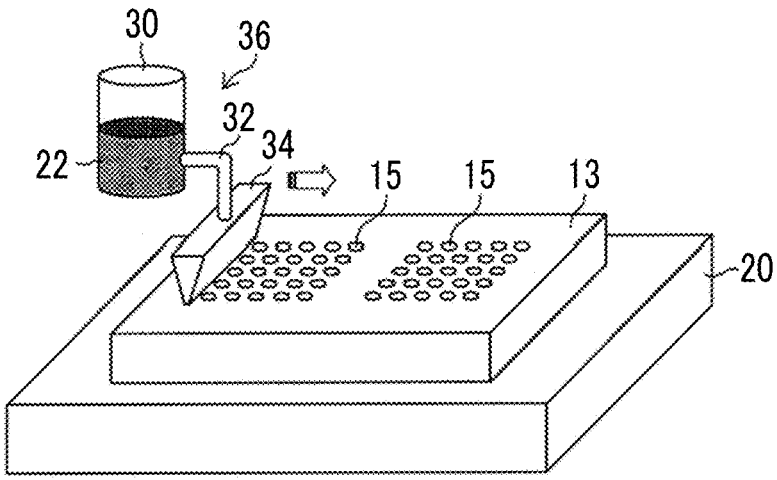
FIGS. 12A to 12C are views schematically illustrating a step of filling the mold with a polymer-dissolved solution containing a drug, a liposome, and a salt.

As illustrated in FIG. 12A, the mold 13 having needle-like recesses 15 which are two-dimensionally arranged is disposed on a base 20. In the mold 13, two sets of plural needle-like recesses 15 are formed such that 5 rows of needle-like recesses 15 and 5 columns of needle-like recesses 15 are two-dimensionally arranged. A liquid supply device 36 including a tank 30 which accommodates a water-soluble polymer-dissolved solution 22 containing a drug, a liposome, and a salt; a pipe 32 which is connected with the tank; and a nozzle 34 which is connected with the tip of the pipe 32 is prepared. Further, in the present example, the case where 5 rows of needle-like recesses 15 and 5 columns of needle-like recesses 15 are two-dimensionally arranged is exemplified, but the number of the needle-like recesses 15 is not limited to 5 rows×5 columns as long as the needle-like recesses are two-dimensionally arranged in a manner of M×N (M and N each independently represent an arbitrary integer of 1 or greater, preferably in a range of 2 to 30, more preferably in a range of 3 to 25, and still more preferably in a range of 3 to 20).

Figure 12B:
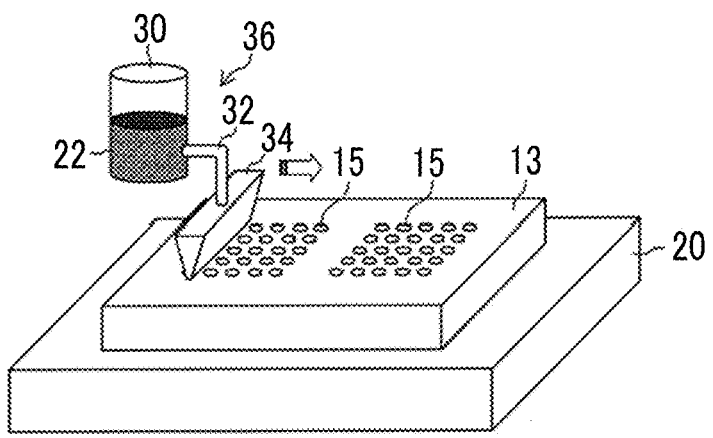
Figure 12C:
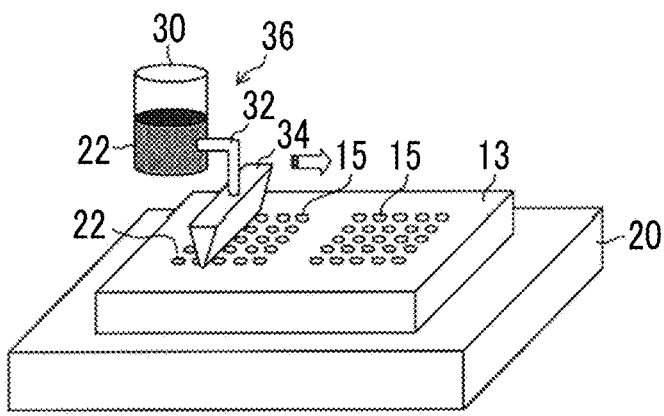
Figure 13:
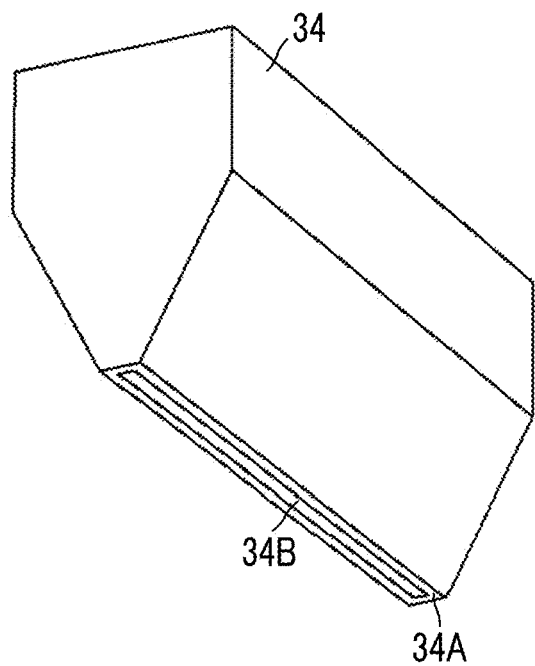
FIG. 13 is a perspective view illustrating the tip of a nozzle.

FIG. 13 is a perspective view schematically illustrating the tip portion of the nozzle. As illustrated in FIG. 12, the tip of the nozzle 34 includes a lip portion 34A which is a flat surface and an opening portion 34B having a slit shape. For example, a plurality of needle-like recesses 15 forming one row can be concurrently filled with the water-soluble polymer-dissolved solution 22 containing a drug, a liposome, and a salt because of the opening portion 34B having a slit shape. The size (the length and the width) of the opening portion 34B can be suitably selected according to the number of needle-like recesses 15 to be filled with the water-soluble polymer-dissolved solution at the same time. When the length of the opening portion 34B is set to be large, a larger amount of needle-like recesses 15 can be filled with the polymer-dissolved solution 22 containing a drug, a liposome, and a salt at the same time. In this manner, the productivity can be improved.

As the material used for the nozzle 34, an elastic material or a metal material can be used. Examples thereof include TEFLON (registered trademark), stainless steel (steel special use stainless (SUS)), and titanium.

As illustrated in FIG. 12B, the position of the opening portion 34B of the nozzle 34 is adjusted on the needle-like recesses 15. The lip portion 34A of the nozzle 34 is in contact with the surface of the mold 13. The water-soluble polymer-dissolved solution 22 containing a drug, a liposome, and a salt is supplied to the mold 13 from a liquid supply device 36, and the water-soluble polymer-dissolved solution 22 containing a drug, a liposome, and a salt fills the needle-like recesses 15 from the opening portion 34B of the nozzle 34. In the present embodiment, a plurality of needle-like recesses 15 forming one row can be concurrently filled with the polymer-dissolved solution 22 containing a drug, a liposome, and a salt. However, the present invention is not limited thereto, and the needle-like recesses 15 can be filled with the water-soluble polymer-dissolved solution one by one.

In a case where the mold 13 is formed of a material having a gas permeability, the water-soluble polymer-dissolved solution 22 containing a drug, a liposome, and a salt can be suctioned by suctioning the solution from the rear surface of the mold 13, and the filling of the needle-like recesses 15 with the water-soluble polymer-dissolved solution 22 containing a drug, a liposome, and a salt can be promoted.

Next to the filling step of FIG. 12B, as illustrated in FIG. 12C, the lip portion 34A of the nozzle 34 is brought into contact with the surface of the mold 13, the liquid supply device 36 is relatively moved in the length direction and the vertical direction of the opening portion 34B, and the nozzle 34 is moved to the needle-like recesses 15 which are not filled with the water-soluble polymer-dissolved solution 22 containing a drug, a liposome, and a salt. The position of the opening portion 34B of the nozzle 34 is adjusted on the needle-like recesses 15. In the present embodiment, the example of moving the nozzle 34 has been described, but the mold 13 may be moved.

Since the lip portion 34A of the nozzle 34 is brought into contact with the surface of the mold 13 and then the movement is made, the water-soluble polymer-dissolved solution 22 containing a drug, a liposome, and a salt, which remains on the surface other than the needle-like recesses 15 of the mold 13 can be collected by the nozzle 34. It is possible to prevent the water-soluble polymer-dissolved solution 22 containing a drug, a liposome, and a salt from remaining on the surface other than the needle-like recesses 15 of the mold 13.

In order to reduce the damage to the mold 13 and suppress deformation due to compression of the mold 13 as much as possible, it is preferable that the pressing pressure of the nozzle 34 against the mold 13 is set to be as small as possible during the movement. Further, in order to prevent the water-soluble polymer-dissolved solution 22 containing a drug, a liposome, and a salt from remaining on the surface other than the needle-like recesses 15 of the mold 13, it is preferable that at least one of the mold 13 or the nozzle 34 is formed of a flexible material which can be elastically deformed.

By repeating the filling step of FIG. 12B and the moving step of FIG. 12C, 5 rows and 5 columns of needle-like recesses 15 which are two-dimensionally arranged are filled with the water-soluble polymer-dissolved solution 22 containing a drug, a liposome, and a salt. When 5 rows and 5 columns of needle-like recesses 15 which are two-dimensionally arranged are filled with the water-soluble polymer-dissolved solution 22 containing a drug, a liposome, and a salt, the liquid supply device 36 is moved to 5 rows and 5 columns of two-dimensionally arranged needle-like recesses 15 which are adjacent to the needle-like recesses filled with the solution and then the filling step of FIG. 12B and the moving step of FIG. 12C are repeated. The 5 rows and 5 columns of two-dimensionally arranged needle-like recesses 15 which are adjacent to the needle-like recesses filled with the solution are filled with the water-soluble polymer-dissolved solution 22 containing a drug, a liposome, and a salt.

For the above-described filling step and moving step, (1) embodiment in which the needle-like recesses 15 are filled with the water-soluble polymer-dissolved solution 22 containing a drug, a liposome, and a salt while the nozzle 34 is moved or (2) embodiment in which the nozzle 34 is temporarily stopped on the needle-like recesses 15 during the movement of the nozzle 34, the needle-like recesses 15 are filled with the water-soluble polymer-dissolved solution 22 containing a drug, a liposome, and a salt, and the nozzle 34 is moved again after the filling may be adopted. The lip portion 34A of the nozzle 34 is brought into contact with the surface of the mold 13 between the filling step and the moving step.

Figure 14:
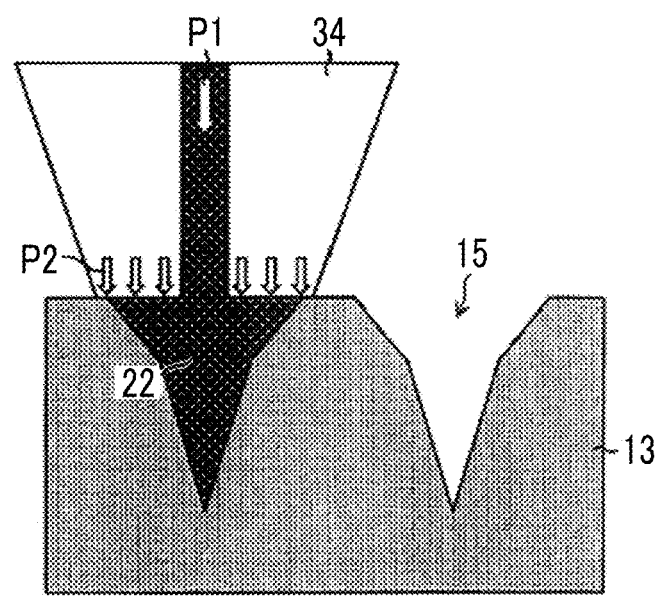
FIG. 14 is a partially enlarged view of the tip of the nozzle and the mold during filling.

FIG. 14 is a partially enlarged view of the mold 13 and the tip of the nozzle 34 at the time of filling the needle-like recess 15 with the water-soluble polymer-dissolved solution 22 containing a drug, a liposome, and a salt. As illustrated in FIG. 14, the filling of the needle-like recess 15 with the water-soluble polymer-dissolved solution 22 containing a drug, a liposome, and a salt can be promoted by applying a pressing pressure P1 into the nozzle 34. Further, when the needle-like recess 15 is filled with the water-soluble polymer-dissolved solution 22 containing a drug, a liposome, and a salt, it is preferable that a pressing force P2 for bringing the nozzle 34 into contact with the surface of the mold 13 is set to be greater than or equal to the pressing pressure P1 applied into the nozzle 34. When the pressing force P2 is set to be greater than or equal to the pressing pressure P1, it is possible to suppress leaking of the water-soluble polymer-dissolved solution 22 containing a drug, a liposome, and a salt to the surface of the mold 13 from the needle-like recess 15.

Figure 15:
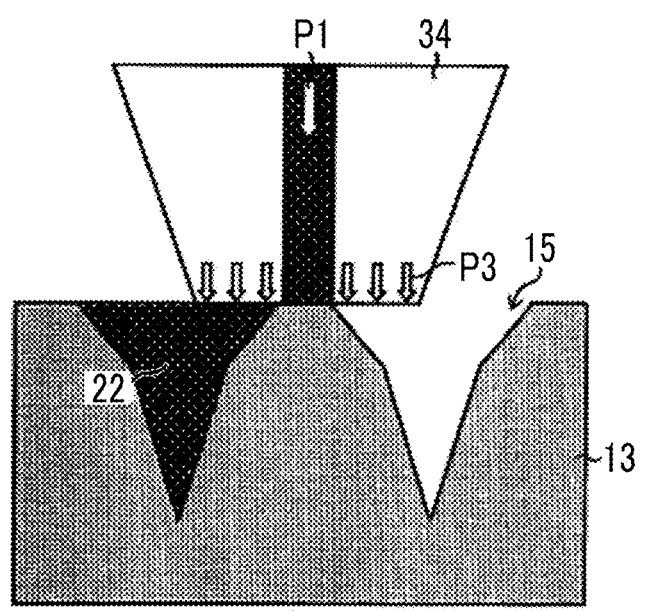
FIG. 15 is a partially enlarged view of the tip of the nozzle and the mold during transfer.

FIG. 15 is a partially enlarged view of the tip of the nozzle 34 and the mold 13 during the movement of the nozzle 34. When the nozzle 34 is relatively moved with respect to the mold 13, it is preferable that a pressing force P3 of bringing the nozzle 34 into contact with the surface of the mold 13 is set to be smaller than the pressing force P2 of bringing the nozzle 34 into contact with the surface of the mold 13 during the filling. When the pressing force P3 is set to be smaller than the pressing force P2, the damage to the mold 13 is reduced and the deformation of the mold 13 due to compression is suppressed.

When the filling of the plurality of needle-like recesses 15 formed of 5 rows and 5 columns of needle-like recesses is completed, the nozzle 34 is moved to the plurality of needle-like recesses 15 formed of 5 rows and 5 columns of needle-like recesses adjacent to the needle-like recesses filled with the solution. When the nozzle 34 is moved to the plurality of needle-like recesses 15 formed of 5 rows and 5 columns of needle-like recesses adjacent to the needle-like recesses filled with the solution at the time of liquid supply, it is preferable that the supply of the water-soluble polymer-dissolved solution 22 containing a drug, a liposome, and a salt is stopped. There is a distance between the needle-like recesses 15 in the fifth row and the needle-like recesses 15 in the next first row. When the water-soluble polymer-dissolved solution 22 containing a drug, a liposome, and a salt is continuously supplied during the movement of the nozzle 34 between the rows, the liquid pressure inside of the nozzle 34 is extremely high in some cases. As the result, the water-soluble polymer-dissolved solution 22 containing a drug, a liposome, and a salt supplied from the nozzle 34 occasionally flows out of the needle-like recesses 15 of the mold 13. In order to suppress the flowing out of the solution, it is preferable that the liquid pressure inside the nozzle 34 is detected and the supply of the water-soluble polymer-dissolved solution 22 containing a drug, a liposome, and a salt is stopped when it is determined that the liquid pressure is extremely high.

In the above, the method of supplying the water-soluble polymer-dissolved solution containing a drug, a liposome, and a salt using a dispenser that has a nozzle has been described, but bar coating, spin coating, or spray coating can be applied in addition to the coating with the dispenser.

In the present invention, it is preferable that the drying treatment is performed after the water-soluble polymer-dissolved solution containing a drug, a liposome, and a salt is supplied to the needle-like recesses.

(Formation of Sheet)

Several embodiments of a step of forming the sheet will be described.

Figure 16A:
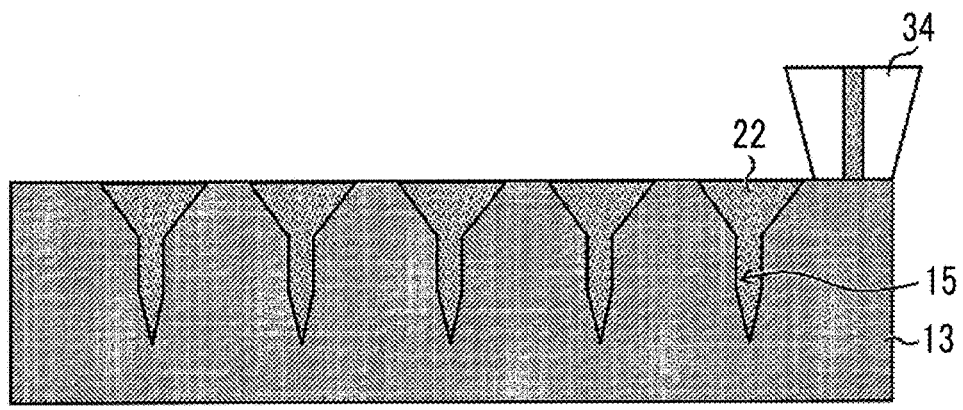
FIGS. 16A to 16D are views describing a step of forming another microneedle array.
Figure 16B:
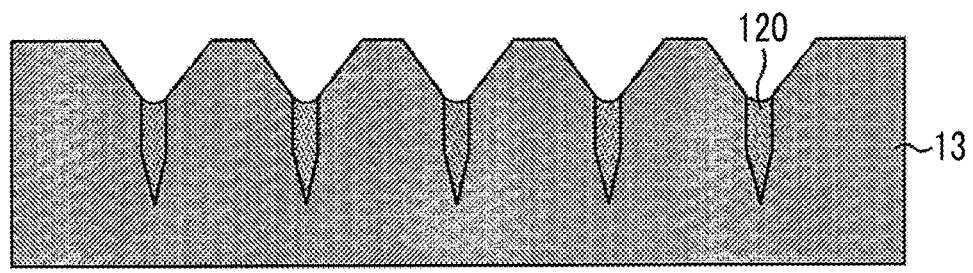
Figure 16C:
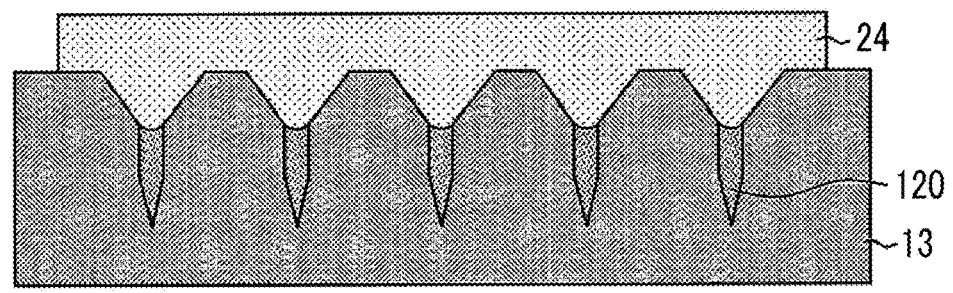
Figure 16D:
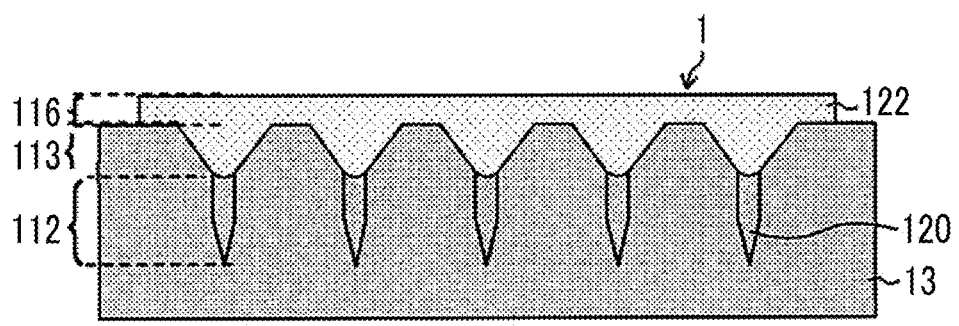

A first embodiment of a step of forming the sheet will be described with reference to FIGS. 16A to 16D. The needle-like recesses 15 of the mold 13 are filled with the water-soluble polymer-dissolved solution 22 containing a drug, a liposome, and a salt from the nozzle 34. Next, a layer 120 containing a drug in the needle-like recesses 15 is formed by drying and solidifying the water-soluble polymer-dissolved solution 22 containing a drug, a liposome, and a salt as illustrated in FIG. 16B. Subsequently, the mold 13 on which the layer 120 containing a drug is formed is coated with the water-soluble polymer-dissolved solution 24 using a dispenser as illustrated in FIG. 16C. In addition to the coating with the dispenser, bar coating, spin coating, or spray coating can be applied. Since the layer 120 containing a drug is solidified, it is possible to suppress the diffusion of the drug in the water-soluble polymer-dissolved solution 24. Next, the microneedle array 1 including a plurality of needles 112, frustums 113, and the sheet 116 is formed by drying and solidifying the water-soluble polymer-dissolved solution 24 as illustrated in FIG. 16D.

In the first embodiment, in order to promote the filling of the needle-like recesses 15 with the water-soluble polymer-dissolved solution 22 and the water-soluble polymer-dissolved solution 24 containing a drug, a liposome, and a salt, it is preferable to apply a pressure from the surface of the mold 13 and perform suctioning from the rear surface of the mold 13 under reduced pressure.

Figure 17A:
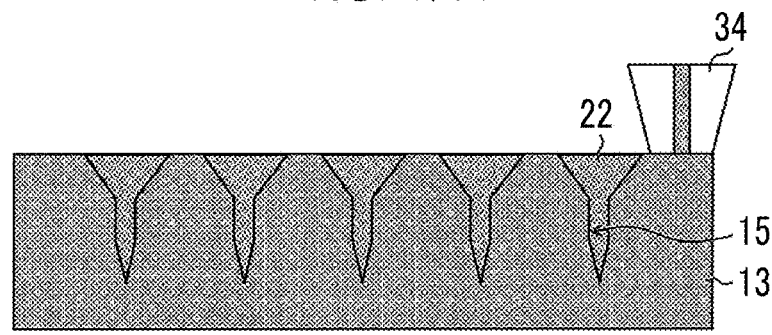
FIGS. 17A to 17C are views describing a step of forming another microneedle array.
Figure 17B:
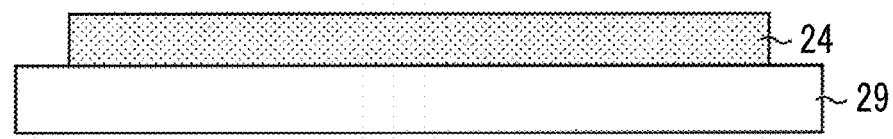
Figure 17C:
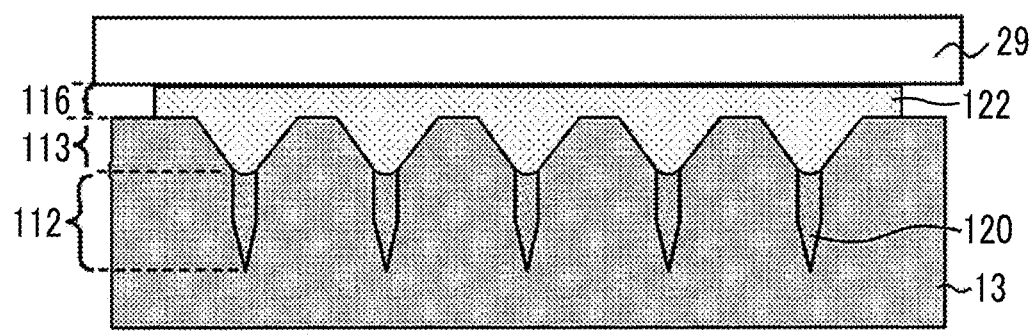

Subsequently, a second embodiment will be described with reference to FIGS. 17A to 17C. The needle-like recesses 15 of the mold 13 are filled with the water-soluble polymer-dissolved solution 22 containing a drug, a liposome, and a salt from the nozzle 34 as illustrated in FIG. 17A. Next, similar to FIG. 16B, the layer 120 containing a drug is formed in the needle-like recesses 15 by drying and solidifying the water-soluble polymer-dissolved solution 22 containing a drug, a liposome, and a salt. Next, another support 29 is coated with the water-soluble polymer-dissolved solution 24 as illustrated in FIG. 17B. The support 29 is not limited, and examples of the support include polyethylene, polyethylene terephthalate, polycarbonate, polypropylene, an acrylic resin, triacetyl cellulose, and glass. Subsequently, the water-soluble polymer-dissolved solution 24 formed on the support 29 overlaps with the mold 13 having the layer 120 containing a drug formed on the needle-like recesses 15 as illustrated in FIG. 17C. In this manner, the needle-like recesses 15 are filled with the water-soluble polymer-dissolved solution 24. Since the layer containing a drug is solidified, it is possible to suppress the diffusion of the drug in the water-soluble polymer-dissolved solution 24. Next, the microneedle array 1 including a plurality of needles 112, frustums 113, and the sheet 116 is formed by drying and solidifying the water-soluble polymer-dissolved solution 24.

In the second embodiment, in order to promote the filling of the needle-like recesses 15 with the water-soluble polymer-dissolved solution 24, it is preferable to apply a pressure from the surface of the mold 13 and perform decompressing and suctioning from the rear surface of the mold 13.

As the method of drying the water-soluble polymer-dissolved solution 24, a step of volatilizing the solvent in the polymer-dissolved solution may be exemplified. The method is not particularly limited, and a method of performing heating, blowing air, or decompression may be used. The drying treatment can be performed under the conditions of 1° C. to 50° C. for 1 to 72 hours. Examples of the method of blowing air include a method of blowing hot air at 0.1 to 10 m/sec. It is preferable that the drying temperature is set to a temperature at which the drug in the water-soluble polymer-dissolved solution 22 containing a drug, a liposome, and a salt is not thermally deteriorated.

(Peeling)

Figure 18:
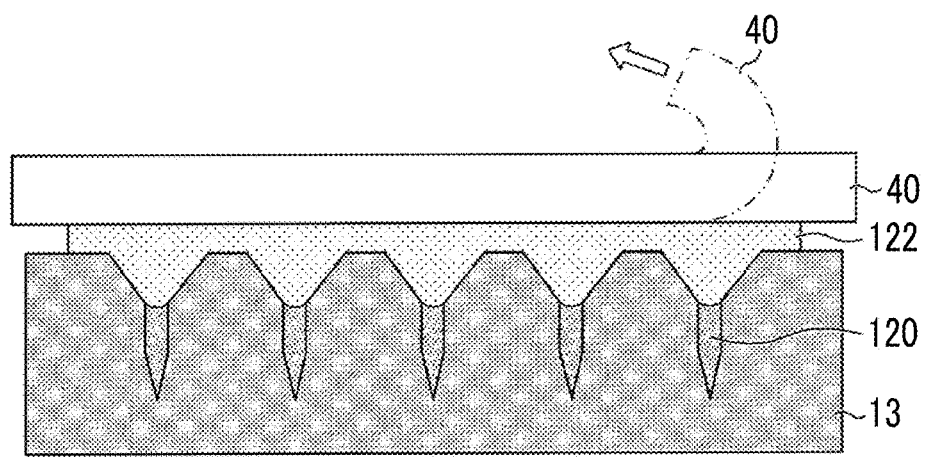
FIG. 18 is a view describing a peeling step.
Figure 19:
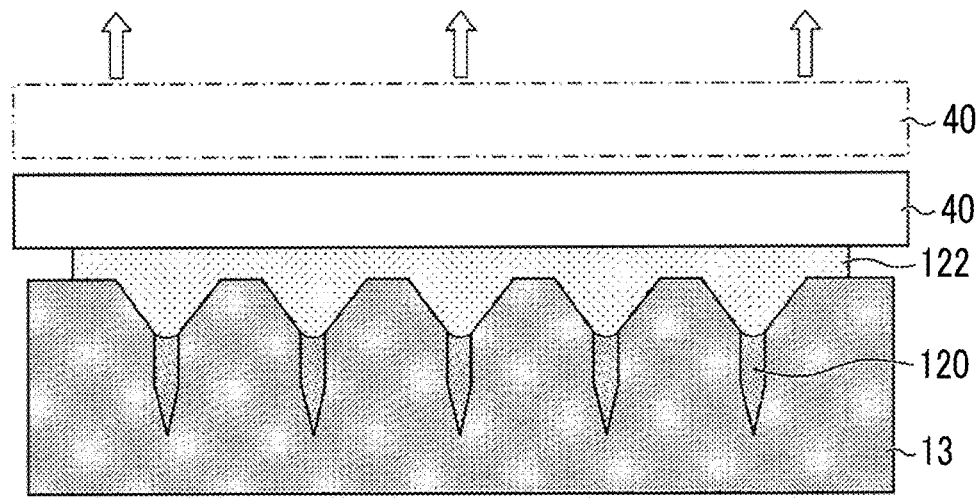
FIG. 19 is a view describing another peeling step.

A method of peeling the microneedle array from the mold 13 is not particularly limited. It is preferable that needle projections are not bent or broken at the time of peeling. Specifically, a sheet-like base material 40 on which a pressure sensitive adhesive layer is formed is attached to the microneedle array and then the base material 40 can be peeled off from the end portion such that the base material 40 is turned over as illustrated in FIG. 18. However, the needle projections can be bent when this method is used. Therefore, as illustrated in FIG. 19, a sucking disc (not illustrated) is disposed on the base material 40 on the microneedle array so that a method of vertically pulling the base material up while suctioning the base material with air can be applied. Further, the support 29 may be used as the base material 40.

Figure 20:
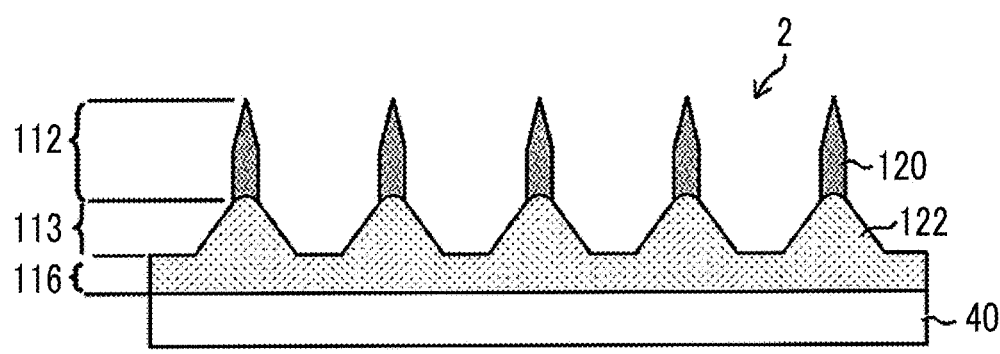
FIG. 20 is a view describing a microneedle array.

FIG. 20 illustrates the microneedle array 2 peeled from the mold 13. The microneedle array 2 includes the base material 40, the needles 112 formed on the base material 40, the frustums 113, and the sheet 116. At least the tip of the needle 112 has a conical shape or a polygonal pyramid shape, but the shape of the needle 112 is not limited thereto.

Hereinafter, the present invention will be described in detail with reference to examples. The materials, the amounts to be used, the ratios, the treatment contents, and the treatment procedures shown in the examples described below can be appropriately changed as long as they are within the gist of the present invention. Accordingly, the scope of the present invention should not be limitatively interpreted by the specific examples described below.

EXAMPLES

The abbreviations in the examples are as follows.

PC: phosphatidylcholine [COATSOME (registered trademark) NC-21E (manufactured by NOF Corporation) were used in the examples other than Example 6 and the comparative examples other than Comparative Example 7, and COATSOME (registered trademark) NC-20 (manufactured by NOF Corporation) were used in Example 6 and Comparative Example 7]

Chol: cholesterol

DSPG: distearoyl phosphatidylglycerol

HES: hydroxyethyl starch

DEX: dextran

CS: sodium chondroitin sulfate

<Evaluation of Filtration Property of Liquid Containing Water-Soluble Polymer and Liposomes>

(Preparation of 10 mmol/L (pH of 7) of Phosphoric Acid Aqueous Solution)

159 mg of sodium dihydrogen phosphate dihydrate (Merch KGaA) and 174 mg of disodium hydrogen phosphate dihydrate (Merch KGaA) were dissolved in 200 mL of water for injection, thereby preparing 10 mmol/L (pH of 7) of a phosphoric acid aqueous solution.

(Preparation of Liposomes)

The lipids listed in Table 1 were dissolved in chloroform to have the mass ratio listed in Table 1 and the thickness of the membrane was reduced. Next, 10 mmol/L (pH of 7) of the phosphoric acid aqueous solution was added for hydration.

The obtained mixture was irradiated with ultrasonic waves and sized to have a particle diameter of 100 nm. The obtained product was filtered using a polyvinylidene difluoride (PDVF) having pore diameter of 0.22 µm, thereby preparing liposomes.

(Measurement of Zeta Potential)

The prepared liposomes were diluted to 0.1 mg/mL with 10 mmol/L (pH of 7) of the phosphoric acid aqueous solution, and the zeta potential of the obtained solution was measured. The zeta potential was measured using ELS-Z2 (manufactured by Otsuka Electronics Co., Ltd.).

(Evaluation of Mixing Liposomes with Water-Soluble Polymer and Filtration Property)

A water-soluble polymer (the type thereof is listed in Table 1) and a salt (the type thereof is listed in Table 1) were dissolved in 10 mmol/L (pH of 7) of the phosphoric acid aqueous solution. Subsequently, the liposomes (the type thereof is listed in Table 1) prepared in the above-described manner, the water-soluble polymer (the type thereof is listed in Table 1), and the salt (the type thereof is listed in Table 1) were mixed such that the concentration of the liposomes was set to 1% by mass, the concentration of the water-soluble polymer was set to 4% by mass, and the amount of the salt was set to the amount listed in Table 1. The obtained mixture was filtered using a polyvinylidene fluoride (PVDF) filter having a pore diameter of 0.22 µm. The ratio between the liposome concentrations before and after the filtration using the filter was quantified by high performance liquid chromatography (HPLC). The results were evaluated based on the following determination standard. The filtration property was evaluated as A in a case where 90% or greater of the mixture was allowed to pass through the filter, the filtration property was evaluated as B in a case where 90% or greater of the mixture was allowed to pass through the filter even though the mixture was coarse, and the filtration property was evaluated as C in a case where less than 90% of the mixture was allowed to pass through the filter. The results are listed in Table 1.

(Content of Salt)

The content of the salt was calculated by adding the content of an inorganic salt. For example, since the amount of $Na^+$ is 15 mmol/L and the amount of $PO_4^{3-}$ is 10 mmol/L in a case of 10 mmol/L (pH of 7) of phosphoric acid, the total amount thereof is 25 mmol/L. Further, since the amount of $Na^+$ is 150 mmol/L and the amount of $Cl^-$ is 150 mmol/L in a case of 150 mmol/L of NaCl, the total amount thereof is 300 mmol/L. In consideration of forming microneedles, the content of the salt was calculated as the ratio "salt/solid content" with respect to the amount of the solid content in the mixed solution. The total solid content concentration of the mixed solution is 5% by mass since the content of the liposomes is 1% by mass and the content of the water-soluble polymer is 4% by mass. Since the density of the mixed solution is 1.0 g/cm³, the solid content concentration is 50 g/L. Accordingly, in Comparative Example 1 listed in Table 1, since the amount of the salt is 325 mmol/L and the amount of the solid content is 50 g/L, "salt/solid content=325÷50+6.5 mol/g" is satisfied. The calculation results are listed in Table 1.

TABLE 1

| | Liposomes | | | | | | | Evaluation |
|---|---|---|---|---|---|---|---|---|
| | | Concentration of lipids (mass ratio) | | | Zeta | Water-soluble | | Salt/solid content | of filtration |
| | PC | PC | Chol | DSPG | potential | polymer | Salt (after mixing) | (mmol/g) | property |
| Comparative Example 1 | NC-21E | 80 | 20 | 0 | 0 mv | HES | 10 mmol/L of phosphoric acid and 150 mmol/L NaCl | 6.5 | C |
| Comparative Example 2 | NC-21E | 80 | 20 | 0 | 0 mV | HES | Only 10 mmol/L of phosphoric acid | 0.5 | C |
| Comparative Example 3 | NC-21E | 80 | 20 | 1 | −7 mV | HES | Only 10 mmol/L of phosphoric acid | 0.5 | C |
| Example 1 | MC-21E | 80 | 20 | 2 | −12 mV | HES | Only 10 mmol/L of phosphoric acid | 0.5 | A |
| Example 2 | NC-21E | 80 | 20 | 5 | −30 mV | HES | Only 10 mmol/L of phosphoric acid | 0.5 | A |
| Example 3 | NC-21E | 80 | 20 | 10 | −60 mV | HES | Only 10 mmol/L of phosphoric acid | 0.5 | A |
| Comparative Example 4 | NC-21E | 80 | 20 | 5 | −30 mV | HES | 10 mmol/L of phosphoric acid and 150 mmol/L NaCl | 6.5 | C |
| Comparative Example 5 | NC-21E | 80 | 20 | 5 | −30 mV | HES | 10 mmol/L of phosphoric acid and 150 mmol/L KCl | 6.5 | C |
| Example 4 | NC-21E | 80 | 20 | 5 | −30 mV | HES | 10 mmol/L of phosphoric acid and 50 mmol/L NaCl | 2.5 | A |
| Comparative Example 6 | NC-21E | 80 | 20 | 5 | −30 mV | HES | 10 mmol/L of phosphoric acid and 100 mmol/L NaCl | 4.5 | C |
| Example 5 | NC-21E | 80 | 20 | 5 | −30 mV | DEX | Only 10 mmol/L of phosphoric acid | 0.5 | A |
| Example 6 | NC-20 | 80 | 20 | 5 | −30 mV | HES | Only 10 mmol/L of phosphoric acid | 0.5 | A |
| Comparative Example 7 | NC-20 | 80 | 20 | 5 | −30 mV | HES | 10 mmol/L of phosphoric acid and 150 mmol/L KCl | 6.5 | B |

Production and Evaluation of Microneedle Array (Production of Mold)

Figure 21A:
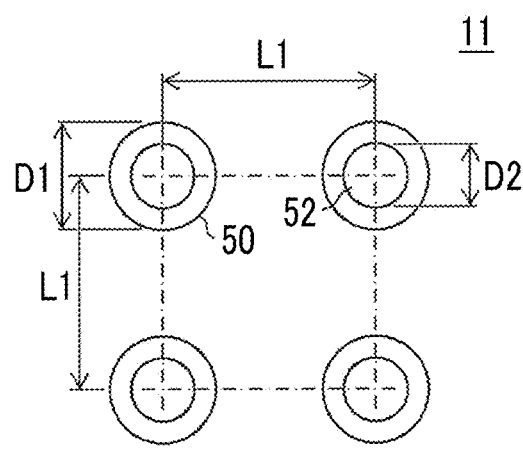
FIGS. 21A and 21B are respectively a plan view and a side view of an original plate.
Figure 21B:
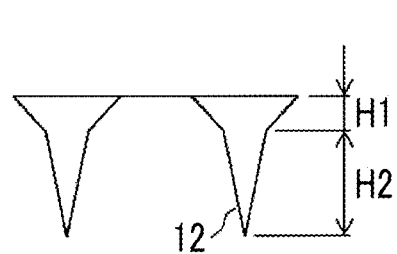

An original plate 11 was prepared by arranging shaped portions 12 having a needle-like structure, on which a cone 52 with a diameter D2 of 300 μm and a height H2 of 500 μm was formed, as illustrated in FIG. 21, on a truncated cone 50 having a bottom surface with a diameter D1 of 500 μm and having a height H1 of 150 μm on the surface of a smooth Ni plate in which each side had a length of 40 mm and performing grinding processing on 100 needles having a pitch L1 of 1000 μm and a square pyramid shape in a two-dimensional square array. The original plate 11 was covered by silicon rubber (SILASTIC MDX 4-4210, manufactured by Dow Corning Toray Co., Ltd.) to form a film having a thickness of 0.6 mm and the film was thermally cured in a state in which 50 μm of the conical tip of the original plate 11 protruded from the film surface and then peeled off. In this manner, an inverted product of the silicon rubber having a through-hole with a diameter of approximately 30 μm was prepared. The silicon rubber inverted product which had 10 rows and 10 columns of needle-like recesses that were two-dimensionally arranged and formed on the central portion and in which the portion other than the flat surface portion in which each side had a length of 30 mm was cut off was used as a mold. A surface on which the opening portion of a needle-like recess was wide was set to the surface of the mold and a surface having a through-hold (air vent hole) with a diameter of 30 μm was set to the rear surface of the mold.

(Liposomes)

Liposomes with the same composition as that in each comparative example and each example listed in Table 1 were prepared.

(Preparation of Polymer-Dissolved Solution Containing Drug, Liposome, and Salt)

Each liposome listed in Table 1, each water-soluble polymer (hydroxyethyl starch (HES) (manufactured by Fresenius Kabi), DEX or CS) listed in Table 1, and Evans Blue (coloring agent: model drug) were mixed at a mass ratio of 1:4:0.1 to prepare an aqueous solution, thereby obtaining a water-soluble polymer-dissolved solution containing a drug, a liposome, and a salt. The concentrations of the liposome, the hydroxyethyl starch, and Evans Blue in the obtained aqueous solution were respectively 1% by mass, 4% by mass, and 0.1% by mass.

(Preparation of Water-Soluble Polymer-Dissolved Solution Forming Sheet)

Dextran was dissolved in water such that the content thereof was set to 40% by mass to prepare a 40 mass % aqueous solution of dextran.

(Filling and Drying of Water-Soluble Polymer-Dissolved Solution Containing Drug, Liposome, and Salt)

0.3 mL of a water-soluble polymer-dissolved solution containing a drug, a liposome, and a salt was added dropwise onto a hole pattern arrangement of a mold having conical recesses, and the mold was placed in a pressure resistant container. Compressed air was injected from a compressor into the pressure resistant container, and the inside of the pressure resistant container was held at a pressure of 0.35 MPa for 5 minutes. By applying the pressure in this manner, air bubbles were removed, and the tip of a needle of the mold was able to be filled with the water-soluble polymer-dissolved solution containing a drug, a liposome, and a salt. After the filling, the extra water-soluble polymer-dissolved solution containing a drug, a liposome, and a salt remaining on the needle hole opening pattern of the mold was recovered and dried at 25° C. for 1 hour.

(Formation and Drying Sheet)

0.1 g of a water-soluble polymer-dissolved solution forming a sheet was added dropwise onto the needle hole opening pattern of the mold obtained by being filled with the water-soluble polymer-dissolved solution containing a drug, a liposome, and a salt and drying the solution, and the mold was placed in a pressure resistant container. Compressed air was injected from a compressor into the pressure resistant container, and the inside of the pressure resistant container was held at a pressure of 0.35 MPa for 5 minutes. By applying the pressure in this manner, air bubbles were removed, the needle of the mold which has been filled with the water-soluble polymer-dissolved solution containing a drug, a liposome, and a salt in advance was able to be brought into close contact with the layer of the water-soluble polymer-dissolved solution, and thus a two-layer type microneedle array formed of a needle and a sheet was able to be formed. Further, since the mold has a bank, the water-soluble polymer-dissolved solution forming the sheet does not protrude from the mold at the time of pressurization. The mold was taken out from the pressure resistant container, put into an oven, and was subjected to a drying treatment at 35° C. for 18 hours.

(Peeling Step)

The dried and solidified microneedle array was carefully peeled off from the mold to form a microneedle array formed of a needle and a sheet.

As described above, in each microneedle array prepared using each liposome listed in Table 1, each water-soluble polymer listed in Table 1, and Evans Blue, the zeta potential of the liposome is as listed in Table 1 and the content of the salt in a portion of a needle containing the liposome is as listed in Table 1.

(Evaluation)

FIG. 22A shows the appearance of the microneedle array produced using the formulation of Comparative Example 7 and FIG. 22B shows the appearance of the microneedle array prepared using the formulation of Example 1.

In the microneedle array (FIG. 22A) of the comparative example in which the content of the salt in the tip of a needle containing the liposome was greater than 2.5 mmol/g, the coloring agent was diffused to a lower portion of the needle. Meanwhile, in the microneedle array (FIG. 22B) of the present invention in which the content of the salt in the tip of a needle containing the liposome was 2.5 mmol/g or less, the coloring agent was concentrated to the tip of a needle, and diffusion of the coloring agent to a lower portion of the needle was not found. As described above, with the configuration of the present invention, it was shown that the tip of a needle was able to be filled with a drug (coloring agent).

With respect to those which had been evaluated as A (90% or greater of the mixture was allowed to pass) and B (90% or greater of the mixture was allowed to pass even though the mixture was coarse) on the filtration, listed in Table 1, the appearance of the microneedle array prepared using the formulation of each comparative example and each example was evaluated by observing whether the coloring agent was diffused to the frustum 113 in the same manner as described above.

The appearance was evaluated as B in a case where the coloring agent was diffused to the frustum 113 similar to Comparative Example 7 shown in FIG. 22A, and the appearance was evaluated as A in a case where the coloring agent was concentrated on the needle 112 similar to Example 1 shown in FIG. 22B and diffusion of the coloring agent to the frustum 113 was not found. The results of the evaluation are listed in Table 2.

TABLE 2

| | Evaluation on filling tip of needle with coloring agent |
|---|---|
| Example 1 | A |
| Example 2 | A |
| Example 3 | A |
| Example 4 | A |
| Example 5 | A |
| Example 6 | A |
| Example 7 | B |

EXPLANATION OF REFERENCES

1: microneedle array
2: microneedle array
110: microneedle
112: needle
112A: first layer of needle
112B: second layer of needle
113: frustum
116: sheet
120: layer containing drug
122: layer which does not contain drug
W: diameter (width)
H: height
T: height (thickness)
11: original plate
12: shaped portion
13: mold
15: needle-like recess
15A: inlet portion
15B: tip recess
15C: air vent hole
D: diameter (diameter)
18: mold complex
19: air permeating sheet
20: base
22: water-soluble polymer-dissolved solution containing drug, liposome, and salt
24: water-soluble polymer-dissolved solution
29: support
30: tank
32: pipe
34: nozzle
34A: lip portion
34B: opening portion
36: liquid supply device
P1: pressing pressure
P2: pressing force
P3: pressing force
40: base material
50: truncated cone
52: cone
D1: diameter
D2: diameter L1: pitch
H1: height
H2: height

What is claimed is:

1. A microneedle array comprising:

a sheet; and a plurality of needles which are present on an upper surface of the sheet, wherein each needle is formed from a solution which contains a water-soluble polymer, a drug, a liposome, and a salt, and the drug is localized at a tip of the needle, a zeta potential of the liposome is −10 mV or less, the zeta potential is a zeta potential of a liquid obtained by diluting the liposome to 0.1 mg/mL with 10 mmol/L of a phosphoric acid aqueous solution having a pH of 7, a content of the salt in a portion of each needle which contains the liposome is 2.5 mmol/g or less, the liposome contains an anionic compound, the anionic compound is at least one selected from the group consisting of phosphatidylglycerol, phosphatidylserine, phosphatidic acid, a lipid containing a polyoxyethylene chain, and a saponin, and the water-soluble polymer is at least one selected from the group consisting of polyethylene glycol, polyvinylpyrrolidone, dextran, dextrin, hydroxyethyl starch, and a cellulose derivative.

2. The microneedle array according to claim 1, wherein the water-soluble polymer is electrically neutral.

3. The microneedle array according to claim 1, wherein the water-soluble polymer is hydroxyethyl starch, and the liposome contains phosphatidylcholine and distearoyl phosphatidylglycerol.

4. The microneedle array according to claim 1, wherein the drug is a hormone or a vaccine.

5. The microneedle array according to claim 1, wherein the salt is a salt containing at least one selected from the group consisting of a sodium ion, a potassium ion, an ammonium ion, a lithium ion, and a silver ion.

6. The microneedle array according to claim 1, wherein the zeta potential of the liposome is from −10 mV to −100 mV.

7. The microneedle array according to claim 1, wherein the content of the salt in a portion of each needle which contains the liposome is from 0.01 mmol/g to 2.5 mmol/g.

8. The microneedle array according to claim 1, wherein the zeta potential of the liposome is of a value effective to suppress aggregation of liposomes.

9. The microneedle array according to claim 1, wherein the zeta potential of the liposome is of a value effective to suppress aggregation of liposomes in a case where a water-soluble polymer is mixed with liposomes during production of the microneedle array.

10. The microneedle array according to claim 1, wherein the zeta potential of the liposome results in suppressing aggregation of liposomes.

11. The microneedle array according to claim 1, wherein the zeta potential of the liposome results in suppressing aggregation of liposomes in a case where a water-soluble polymer is mixed with liposomes during production of the microneedle array.

12. A microneedle array comprising:

a sheet; and a plurality of needles which are present on an upper surface of the sheet, wherein each needle is formed from a solution which contains a water-soluble polymer, a drug, a liposome, and a salt, and the drug is localized at a tip of the needle, the zeta potential of the liposome is in a range from −10 mV to −100 mV and is of a value effective to suppress aggregation of liposomes, the zeta potential is a zeta potential of a liquid obtained by diluting the liposome to 0.1 mg/mL with 10 mmol/L of a phosphoric acid aqueous solution having a pH of 7, the content of the salt in a portion of each needle which contains the liposome is from 0.01 mmol/g to 2.5 mmol/g, the liposome contains an anionic compound, the anionic compound is at least one selected from the group consisting of phosphatidylglycerol, phosphatidylserine, phosphatidic acid, a lipid containing a polyoxyethylene chain, and a saponin, and the water-soluble polymer is at least one selected from the group consisting of polyethylene glycol, polyvinylpyrrolidone, dextran, dextrin, hydroxyethyl starch, and a cellulose derivative.

13. The microneedle array according to claim 12, wherein the water-soluble polymer is electrically neutral.

14. The microneedle array according to claim 12, wherein the water-soluble polymer is hydroxyethyl starch, and the liposome contains phosphatidylcholine and distearoyl phosphatidylglycerol.

15. The microneedle array according to claim 12, wherein the drug is a hormone or a vaccine.

16. The microneedle array according to claim 12, wherein the zeta potential of the liposome results in suppressing aggregation of liposomes in a case where a water-soluble polymer is mixed with liposomes during production of the microneedle array.

* * * * *